(12) United States Patent
Guy et al.

(10) Patent No.: US 8,088,893 B2
(45) Date of Patent: Jan. 3, 2012

(54) HYPOXIA INDUCING FACTORS AND USES THEREOF FOR INDUCING ANGIOGENESIS AND IMPROVING MUSCULAR FUNCTIONS

(75) Inventors: Louis-Georges Guy, Montréal (CA); Anouk Fortin, Ottawa (CA)

(73) Assignee: Angiogene Inc., Quebec (CA)

( * ) Notice: Subject to any disclaimer, the term of this patent is extended or adjusted under 35 U.S.C. 154(b) by 0 days.

(21) Appl. No.: 12/400,955

(22) Filed: Mar. 10, 2009

(65) Prior Publication Data

US 2009/0246180 A1 Oct. 1, 2009

Related U.S. Application Data

(62) Division of application No. 10/154,386, filed on May 23, 2002, now Pat. No. 7,608,698.

(60) Provisional application No. 60/292,630, filed on May 23, 2001, provisional application No. 60/354,529, filed on Feb. 8, 2002.

(51) Int. Cl.
  *A61K 38/00* (2006.01)
  *A61K 38/16* (2006.01)
  *A61K 38/17* (2006.01)

(52) U.S. Cl. .......................... 530/350; 514/1.1; 514/13.3

(58) Field of Classification Search ........................ None
See application file for complete search history.

(56) References Cited

U.S. PATENT DOCUMENTS

| 5,882,914 A | 3/1999 | Semenza | |
|---|---|---|---|
| 6,562,799 B1 * | 5/2003 | Semenza | 514/44 R |

FOREIGN PATENT DOCUMENTS

| WO | WO9928464 | 6/1999 |
| WO | WO0009657 | 2/2000 |
| WO | WO 00/29437 A1 | 5/2000 |

OTHER PUBLICATIONS

Gu YZ et al., "Molecular Characterization and Chromosomal Localization of a Third Alpha-Class Hypoxia Inducible Factor Subunit, HIF3ALPHA", Gene Expr 1998; 7(3): 205-13.

Kietzmann T. et al., "Perivenous Expression of the mRNA of the Three Hypoxia-Inducible Factor Alpha-Subunits, HIF3ALPHA, HIF2ALPHA and HIF3ALPHA, in Rat Liver", Biochem J 2001, Mar. 15;354 (Pt 3): 531-7.

Hara S. et al., "Expression and Characterization of Hypoxia-Inducible Factor (HIF)-3ALPHA in Human Kidney: Suppression of HIF-Mediated Gene Expression by HIF-3ALPHA", Biochem Biophys Res Commun 2001, Oct. 5;287(4): 808-13.

One page corresponding to GENBANK™, accession No. AF079154 (Jan. 1, 1999).

One page corresponding to GENBANK™, accession No. AAC99397 (Jan. 1, 1999).

Two pages corresponding to GENBANK™, accession No. AB054067 (Jan. 18, 2002).

International Search Report corresponding to PCT/CA02/00752 mailed Dec. 11, 2002.

Lamerdin, Je, et al. "Putative Homolog of Hypoxia Inducible Factor Three Alpha" *Database SWALL* Database accession No. Q9Y2N7. Online. Abstract only. (Nov. 12, 1999).

Strausberg, Robert. "Homo sapiens cDNA Clone IMAGE:2960025" *Database EMBL* Database accession No. BE250712. Online. Abstract only. (Jul. 14, 2000).

Bagowski et al. "Cell-Type Specific Phosphorylation of Threonines T654 and T669 by PKD Defines the Signal Capacity of the EGF Receptor" *The EMBO Journal* 18(20):5567-5576 (1999).

Fischer et al. "Toll-Like Receptor 9 Signaling Can Sensitize Fibroblasts for Apoptosis" *Immunology Letters* 97:115-122 (2005).

Tian et al. "Endothelial PAS Domain Protein 1 (EPAS1), a Transcription Factor Selectively Expressed in Endothelial Cells" *Genes and Development* 11(1):72-82 (1997).

Wiesener et al. "Widespread, Hypoxia-Inducible Expression of HIF-2α in Distinct Cell Populations of Different Organs" *The FASEB Journal* 17(2):271-292 (2002).

\* cited by examiner

*Primary Examiner* — Jennifer Dunston
(74) *Attorney, Agent, or Firm* — Myers Bigel Sibley & Sajovec, P.A.

(57) ABSTRACT

This invention provides HIF-3α nucleic acid and protein sequences. Also provided are methods for using HIF-3α nucleic acids, proteins, fragments, antibodies, probes, and cells, to characterize HIF-3α, modulate HIF-3α cellular levels, induce angiogenesis, improve muscular function, and treat coronary and cardiac diseases in mammals.

3 Claims, 11 Drawing Sheets

SEQUENCE LISTING

<160> NUMBER OF SEQ ID NOS: 13

<210> SEQ ID NO 1
<211> LENGTH: 2223
<212> TYPE: DNA
<213> ORGANISM: Homo sapiens
<220> FEATURE:
<221> NAME/KEY: CDS
<222> LOCATION: (1)..(2115)
<223> OTHER INFORMATION:

<400> SEQUENCE: 1

```
atg gac agg tcg acc acg gag ctg cgc aag gaa aag tcc cgg gat gcg       48
Met Asp Arg Ser Thr Thr Glu Leu Arg Lys Glu Lys Ser Arg Asp Ala
1               5                   10                  15 gcc cgc agc cgg cgc agc cag gag acc gag gtg ctg tac cag ctg gct       96
Ala Arg Ser Arg Arg Ser Gln Glu Thr Glu Val Leu Tyr Gln Leu Ala
            20                  25                  30 cac acg ctg ccc ttc gcc cgc ggc gtc agc gcc cac ctg gac aag gcc      144
His Thr Leu Pro Phe Ala Arg Gly Val Ser Ala His Leu Asp Lys Ala
        35                  40                  45 tct atc atg cgc ctc acc atc agc tac ctg cgc atg cac cgc ctc tgc      192
Ser Ile Met Arg Leu Thr Ile Ser Tyr Leu Arg Met His Arg Leu Cys
    50                  55                  60 gcc gca ggg gag tgg aac cag gtg gga gca ggg gga gaa cca ctg gat      240
Ala Ala Gly Glu Trp Asn Gln Val Gly Ala Gly Gly Glu Pro Leu Asp
65                  70                  75                  80 gcc tgc tac ctg aag gcc ctg gag ggc ttc gtc atg gtg ctc acc gcc      288
Ala Cys Tyr Leu Lys Ala Leu Glu Gly Phe Val Met Val Leu Thr Ala
                85                  90                  95 gag gga gac atg gct tac ctg tcg gag aat gtc agc aaa cac ctg ggc      336
Glu Gly Asp Met Ala Tyr Leu Ser Glu Asn Val Ser Lys His Leu Gly
            100                 105                 110 ctc agt cag ctg gag ctc att gga cac agc atc ttt gat ttc atc cac      384
Leu Ser Gln Leu Glu Leu Ile Gly His Ser Ile Phe Asp Phe Ile His
        115                 120                 125 ccc tgt gac caa gag gag ctt cag gac gcc ctg acc ccc caa cag acc      432
Pro Cys Asp Gln Glu Glu Leu Gln Asp Ala Leu Thr Pro Gln Gln Thr
    130                 135                 140 ctg tcc agg agg aag gtg gag gcc ccc acg gag cgg tgc ttc tcc ttg      480
Leu Ser Arg Arg Lys Val Glu Ala Pro Thr Glu Arg Cys Phe Ser Leu
145                 150                 155                 160 cgc atg aag agt acg ctc acc agc cgc ggg cgc acc ctc aac ctc aag      528
Arg Met Lys Ser Thr Leu Thr Ser Arg Gly Arg Thr Leu Asn Leu Lys
                165                 170                 175 gcg gcc acc tgg aag gtg ctg aac tgc tct gga cat atg agg gcc tac      576
Ala Ala Thr Trp Lys Val Leu Asn Cys Ser Gly His Met Arg Ala Tyr
            180                 185                 190 aag cca cct gcg cag act tct cca gct ggg agc cct gac tca gag ccc      624
Lys Pro Pro Ala Gln Thr Ser Pro Ala Gly Ser Pro Asp Ser Glu Pro
        195                 200                 205 ccg ctg cag tgc ccg gtg ctc atc tgc gaa gcc atc ccc cac cca ggc      672
Pro Leu Gln Cys Pro Val Leu Ile Cys Glu Ala Ile Pro His Pro Gly
    210                 215                 220 agc ctg gag ccc cca ctg ggc cga ggg gcc ttc ctc agc cgc cac agc      720
Ser Leu Glu Pro Pro Leu Gly Arg Gly Ala Phe Leu Ser Arg His Ser
225                 230                 235                 240 ctg gac atg aag ttc acc tac tgt gac gac agg att gca gaa gtg gct      768
Leu Asp Met Lys Phe Thr Tyr Cys Asp Asp Arg Ile Ala Glu Val Ala
                245                 250                 255
```

```
ggc tat agt ccc gat gac ctg atc ggc tgt tcc gcc tac gag tac atc      816
Gly Tyr Ser Pro Asp Asp Leu Ile Gly Cys Ser Ala Tyr Glu Tyr Ile
        260                 265                 270 cac gcg ctg gac tcc gac gcg gtc agc aag agc atc cac acc ttg ctg      864
His Ala Leu Asp Ser Asp Ala Val Ser Lys Ser Ile His Thr Leu Leu
    275                 280                 285 agc aag ggc cag gca gta aca ggg cag tat cgc ttc ctg gcc cgg agt      912
Ser Lys Gly Gln Ala Val Thr Gly Gln Tyr Arg Phe Leu Ala Arg Ser
290                 295                 300 ggt ggc tac ctg tgg acc cag acc cag gcc aca gtg gtg tca ggg gga      960
Gly Gly Tyr Leu Trp Thr Gln Thr Gln Ala Thr Val Val Ser Gly Gly
305                 310                 315                 320 cgg ggc ccc cag tcg gag agt atc gtc tgt gtc cat ttt tta atc agc     1008
Arg Gly Pro Gln Ser Glu Ser Ile Val Cys Val His Phe Leu Ile Ser
            325                 330                 335 cag gtg gaa gag acc gga gtg gtg ctg tcc ctg gag caa acg gag caa     1056
Gln Val Glu Glu Thr Gly Val Val Leu Ser Leu Glu Gln Thr Glu Gln
        340                 345                 350 cac tct cgc aga ccc att cag cgg ggc gcc ccc tct cag aag ggc acc     1104
His Ser Arg Arg Pro Ile Gln Arg Gly Ala Pro Ser Gln Lys Gly Thr
    355                 360                 365 cct aac cct ggg gac agc ctt gac acc cct ggc ccc cgg atc ctt gcc     1152
Pro Asn Pro Gly Asp Ser Leu Asp Thr Pro Gly Pro Arg Ile Leu Ala
370                 375                 380 ttc ctg cac ccg cct tcc ctg agc gag gct gcc ctg gcc gct gac ccc     1200
Phe Leu His Pro Pro Ser Leu Ser Glu Ala Ala Leu Ala Ala Asp Pro
385                 390                 395                 400 cgc cgt ttc tgc agc cct gac ctc cgt cgc ctc ctg gga ccc atc ctg     1248
Arg Arg Phe Cys Ser Pro Asp Leu Arg Arg Leu Leu Gly Pro Ile Leu
            405                 410                 415 gat ggg gct tca gta gca gcc act ccc agc acc ccg ctg gcc aca cgg     1296
Asp Gly Ala Ser Val Ala Ala Thr Pro Ser Thr Pro Leu Ala Thr Arg
        420                 425                 430 cac ccc caa agt cct ctt tcg gct gat ctc cca gat gaa cta cct gtg     1344
His Pro Gln Ser Pro Leu Ser Ala Asp Leu Pro Asp Glu Leu Pro Val
    435                 440                 445 ggc acc gag aat gtg cac aga ctc ttc acc tcc ggg aaa gac act gag     1392
Gly Thr Glu Asn Val His Arg Leu Phe Thr Ser Gly Lys Asp Thr Glu
450                 455                 460 gca gtg gag aca gat tta gat ata gct cag atg agg aaa ctg aag ctc     1440
Ala Val Glu Thr Asp Leu Asp Ile Ala Gln Met Arg Lys Leu Lys Leu
465                 470                 475                 480 aga ctg ttg acc aca ggc aca gaa ctc aga agt gat ggt gct ggg act     1488
Arg Leu Leu Thr Thr Gly Thr Glu Leu Arg Ser Asp Gly Ala Gly Thr
            485                 490                 495 tca gcc aag gtc cac cca agt cca agg ctc atc ctc tta cct ccc tcc     1536
Ser Ala Lys Val His Pro Ser Pro Arg Leu Ile Leu Leu Pro Pro Ser
        500                 505                 510 tgc cct ccg cag gat gct gat gct ctg gat ttg gag atg ctg gcc ccc     1584
Cys Pro Pro Gln Asp Ala Asp Ala Leu Asp Leu Glu Met Leu Ala Pro
    515                 520                 525 tac atc tcc atg gat gat gac ttc cag ctc aac gcc agc gag cag cta     1632
Tyr Ile Ser Met Asp Asp Asp Phe Gln Leu Asn Ala Ser Glu Gln Leu
530                 535                 540 ccc agg gcc tac cac aga cct ctg ggg gct gtc ccc cgg ccc cgt gct     1680
Pro Arg Ala Tyr His Arg Pro Leu Gly Ala Val Pro Arg Pro Arg Ala
545                 550                 555                 560 cgg agc ttc cat ggc ctg tca cct cca gcc ctt gag ccc tcc ctg cta     1728
Arg Ser Phe His Gly Leu Ser Pro Pro Ala Leu Glu Pro Ser Leu Leu
            565                 570                 575
```

-continued

```
ccc cgc tgg ggg agt gac ccc cgg ctg agc tgc tcc agc cct tcc aga    1776
Pro Arg Trp Gly Ser Asp Pro Arg Leu Ser Cys Ser Ser Pro Ser Arg
            580                 585                 590 ggg gac ccc tca gca tcc tct ccc atg gct ggg gct cgg aag agg acc    1824
Gly Asp Pro Ser Ala Ser Ser Pro Met Ala Gly Ala Arg Lys Arg Thr
        595                 600                 605 ctg gcc cag agc tca gag gac gag gac gag gga gtg gag ctg ctg gga    1872
Leu Ala Gln Ser Ser Glu Asp Glu Asp Glu Gly Val Glu Leu Leu Gly
    610                 615                 620 gtg aga cct ccc aaa agg tcc ccc agc cca gaa cac gaa aac ttt ctg    1920
Val Arg Pro Pro Lys Arg Ser Pro Ser Pro Glu His Glu Asn Phe Leu
625                 630                 635                 640 ctc ttt cct ctc agc ctg agt ttc ctt ctg aca gga gga cca gcc cca    1968
Leu Phe Pro Leu Ser Leu Ser Phe Leu Leu Thr Gly Gly Pro Ala Pro
                645                 650                 655 ggg agc ctg cag gac ccc agc acc cca ctc ctg aac ctg aat gag ccc    2016
Gly Ser Leu Gln Asp Pro Ser Thr Pro Leu Leu Asn Leu Asn Glu Pro
            660                 665                 670 ctg ggc ctg ggc ccc tca ctg ctc tct ccg tac tca gac gag gac act    2064
Leu Gly Leu Gly Pro Ser Leu Leu Ser Pro Tyr Ser Asp Glu Asp Thr
        675                 680                 685 acc cag ccc ggg ggc ccc ttc cag cca agg gca ggc tca gcc cag gct    2112
Thr Gln Pro Gly Gly Pro Phe Gln Pro Arg Ala Gly Ser Ala Gln Ala
    690                 695                 700 gac tgagccggct cctctcccca tctgccttct cctcccccag aaaggacctc         2165
Asp
705 aaccacactc cacgccggca gccaacgcac aggaggtcct tgccttccgg caccaacg    2223

<210> SEQ ID NO 2
<211> LENGTH: 705
<212> TYPE: PRT
<213> ORGANISM: Homo sapiens

<400> SEQUENCE: 2

Met Asp Arg Ser Thr Thr Glu Leu Arg Lys Glu Lys Ser Arg Asp Ala
1               5                   10                  15

Ala Arg Ser Arg Arg Ser Gln Glu Thr Glu Val Leu Tyr Gln Leu Ala
                20                  25                  30

His Thr Leu Pro Phe Ala Arg Gly Val Ser Ala His Leu Asp Lys Ala
            35                  40                  45

Ser Ile Met Arg Leu Thr Ile Ser Tyr Leu Arg Met His Arg Leu Cys
        50                  55                  60

Ala Ala Gly Glu Trp Asn Gln Val Gly Ala Gly Glu Pro Leu Asp
65                  70                  75                  80

Ala Cys Tyr Leu Lys Ala Leu Glu Gly Phe Val Met Val Leu Thr Ala
                85                  90                  95

Glu Gly Asp Met Ala Tyr Leu Ser Glu Asn Val Ser Lys His Leu Gly
            100                 105                 110

Leu Ser Gln Leu Glu Leu Ile Gly His Ser Ile Phe Asp Phe Ile His
        115                 120                 125

Pro Cys Asp Gln Glu Glu Leu Gln Asp Ala Leu Thr Pro Gln Gln Thr
    130                 135                 140

Leu Ser Arg Arg Lys Val Glu Ala Pro Thr Glu Arg Cys Phe Ser Leu
145                 150                 155                 160

Arg Met Lys Ser Thr Leu Thr Ser Arg Gly Arg Thr Leu Asn Leu Lys
                165                 170                 175

Ala Ala Thr Trp Lys Val Leu Asn Cys Ser Gly His Met Arg Ala Tyr
```

```
                    180                 185                 190
Lys Pro Pro Ala Gln Thr Ser Pro Ala Gly Ser Pro Asp Ser Glu Pro
                195                 200                 205

Pro Leu Gln Cys Pro Val Leu Ile Cys Glu Ala Ile Pro His Pro Gly
            210                 215                 220

Ser Leu Glu Pro Pro Leu Gly Arg Gly Ala Phe Leu Ser Arg His Ser
225                 230                 235                 240

Leu Asp Met Lys Phe Thr Tyr Cys Asp Arg Ile Ala Glu Val Ala
                245                 250                 255

Gly Tyr Ser Pro Asp Leu Ile Gly Cys Ser Ala Tyr Glu Tyr Ile
                260                 265                 270

His Ala Leu Asp Ser Asp Ala Val Ser Lys Ser Ile His Thr Leu Leu
            275                 280                 285

Ser Lys Gly Gln Ala Val Thr Gly Gln Tyr Arg Phe Leu Ala Arg Ser
        290                 295                 300

Gly Gly Tyr Leu Trp Thr Gln Thr Gln Ala Thr Val Val Ser Gly Gly
305                 310                 315                 320

Arg Gly Pro Gln Ser Glu Ser Ile Val Cys Val His Phe Leu Ile Ser
                325                 330                 335

Gln Val Glu Glu Thr Gly Val Val Leu Ser Leu Glu Gln Thr Glu Gln
            340                 345                 350

His Ser Arg Arg Pro Ile Gln Arg Gly Ala Pro Ser Gln Lys Gly Thr
                355                 360                 365

Pro Asn Pro Gly Asp Ser Leu Asp Thr Pro Gly Pro Arg Ile Leu Ala
        370                 375                 380

Phe Leu His Pro Pro Ser Leu Ser Glu Ala Ala Leu Ala Ala Asp Pro
385                 390                 395                 400

Arg Arg Phe Cys Ser Pro Asp Leu Arg Arg Leu Leu Gly Pro Ile Leu
                405                 410                 415

Asp Gly Ala Ser Val Ala Ala Thr Pro Ser Thr Pro Leu Ala Thr Arg
            420                 425                 430

His Pro Gln Ser Pro Leu Ser Ala Asp Leu Pro Asp Glu Leu Pro Val
        435                 440                 445

Gly Thr Glu Asn Val His Arg Leu Phe Thr Ser Gly Lys Asp Thr Glu
    450                 455                 460

Ala Val Glu Thr Asp Leu Asp Ile Ala Gln Met Arg Lys Leu Lys Leu
465                 470                 475                 480

Arg Leu Leu Thr Thr Gly Thr Glu Leu Arg Ser Asp Gly Ala Gly Thr
                485                 490                 495

Ser Ala Lys Val His Pro Ser Arg Leu Ile Leu Leu Pro Pro Ser
            500                 505                 510

Cys Pro Pro Gln Asp Ala Asp Ala Leu Asp Leu Glu Met Leu Ala Pro
        515                 520                 525

Tyr Ile Ser Met Asp Asp Phe Gln Leu Asn Ala Ser Glu Gln Leu
        530                 535                 540

Pro Arg Ala Tyr His Arg Pro Leu Gly Ala Val Pro Arg Pro Arg Ala
545                 550                 555                 560

Arg Ser Phe His Gly Leu Ser Pro Pro Ala Leu Glu Pro Ser Leu Leu
                565                 570                 575

Pro Arg Trp Gly Ser Asp Pro Arg Leu Ser Cys Ser Ser Pro Ser Arg
            580                 585                 590

Gly Asp Pro Ser Ala Ser Ser Pro Met Ala Gly Ala Arg Lys Arg Thr
        595                 600                 605
```

```
Leu Ala Gln Ser Ser Glu Asp Glu Asp Glu Gly Val Glu Leu Leu Gly
            610                 615                 620
Val Arg Pro Pro Lys Arg Ser Pro Ser Pro Glu His Glu Asn Phe Leu
625                 630                 635                 640
Leu Phe Pro Leu Ser Leu Ser Phe Leu Leu Thr Gly Gly Pro Ala Pro
                645                 650                 655
Gly Ser Leu Gln Asp Pro Ser Thr Pro Leu Leu Asn Leu Asn Glu Pro
            660                 665                 670
Leu Gly Leu Gly Pro Ser Leu Leu Ser Pro Tyr Ser Asp Glu Asp Thr
        675                 680                 685
Thr Gln Pro Gly Gly Pro Phe Gln Pro Arg Ala Gly Ser Ala Gln Ala
    690                 695                 700
Asp
705

<210> SEQ ID NO 3
<211> LENGTH: 2115
<212> TYPE: DNA
<213> ORGANISM: Homo sapiens

<400> SEQUENCE: 3
atggacaggt cgaccacgga gctgcgcaag gaaaagtccc gggatgcggc ccgcagccgg      60
cgcagccagg agaccgaggt gctgtaccag ctggctcaca cgctgccctt cgcccgcggc     120
gtcagcgccc acctggacaa ggcctctatc atgcgcctca ccatcagcta cctgcgcatg     180
caccgcctct gcgccgcagg ggagtggaac caggtgggag caggggagga accactggat     240
gcctgctacc tgaaggccct ggagggcttc gtcatggtgc tcaccgccga gggagacatg     300
gcttacctgt cggagaatgt cagcaaacac ctgggcctca gtcagctgga gctcattgga     360
cacagcatct ttgatttcat ccaccccctgt gaccaagagg agcttcagga cgccctgacc     420
ccccaacaga cccgtccag gaggaaggtg gaggccccca cggagcggtg cttctccttg     480
cgcatgaaga gtacgctcac cagccgcggg cgcaccctca acctcaaggc ggccacctgg     540
aaggtgctga actgctctgg acatatgagg gcctacaagc cacctgcgca gacttctcca     600
gctgggagcc ctgactcaga gcccccgctg cagtgcccgg tgctcatctg cgaagccatc     660
ccccacccag gcagcctgga gcccccactg ggccgagggg ccttcctcag ccgccacagc     720
ctggacatga agttcaccta ctgtgacgac aggattgcag aagtggctgg ctatagtccc     780
gatgacctga tcggctgttc cgcctacgag tacatccacg cgctggactc cgacgcggtc     840
agcaagagca tccacaccct tgctgagcaa ggccaggcag taacagggca gtatcgcttc     900
ctggcccgga gtggtggcta cctgtggacc cagacccagg ccacagtggt gtcaggggga     960
cggggccccc agtcggagag tatcgtctgt gtccattttt taatcagcca ggtggaagag    1020
accggagtgg tgctgtccct ggagcaaacg gagcaacact ctcgcagacc cattcagcgg    1080
ggcgccccct ctcagaaggg caccctaac cctggggaca gccttgacac ccctggcccc    1140
cggatccttg ccttcctgca cccgccttcc ctgagcgagg ctgccctggc cgctgacccc    1200
cgccgtttct gcagccctga cctccgtcgc ctcctgggac ccatcctgga tgggcttca    1260 gtagcagcca ctcccagcac cccgctggcc acacggcacc cccaaagtcc tctttcggct    1320
gatctcccag atgaactacc tgtgggcacc gagaatgtgc acagactctt cacctccggg    1380
aaagacactg aggcagtgga gacagattta gatatagctc agatgaggaa actgaagctc    1440
agactgttga ccacaggcac agaactcaga agtgatggtg ctgggacttc agccaaggtc    1500
cacccaagtc caaggctcat cctcttacct ccctcctgcc ctccgcagga tgctgatgct    1560
```

```
ctggatttgg agatgctggc cccctacatc tccatggatg atgacttcca gctcaacgcc    1620
agcgagcagc tacccagggc ctaccacaga cctctggggg ctgtccccg gccccgtgct     1680 cggagcttcc atggcctgtc acctccagcc cttgagccct ccctgctacc ccgctggggg    1740 agtgacccc ggctgagctg ctccagccct tccagagggg acccctcagc atcctctccc     1800
atggctgggg ctcggaagag gaccctggcc cagagctcag aggacgagga cgagggagtg    1860
gagctgctgg gagtgagacc tcccaaaagg tcccccagcc cagaacacga aaactttctg    1920
ctctttcctc tcagcctgag tttccttctg acaggaggac cagccccagg gagcctgcag    1980
gaccccagca ccccactcct gaacctgaat gagcccctgg gcctgggccc ctcactgctc    2040
tctccgtact cagacgagga cactacccag cccgggggcc ccttccagcc aagggcaggc    2100
tcagcccagg ctgac                                                    2115

<210> SEQ ID NO 4
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 4
ttaagatatc gatgacacgt g                                              21

<210> SEQ ID NO 5
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 5
tcagcacgtg tcatcgatat c                                              21

<210> SEQ ID NO 6
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 6
gctagctagg aagttactcc tctc                                           24

<210> SEQ ID NO 7
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 7
ccatggacag gtcgaccacg gagctgcgca agg                                 33

<210> SEQ ID NO 8
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 8
cgcaggcagg tggcttgtag gccct                                          25
```

```
<210> SEQ ID NO 9
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 9
cagctggagc tcattggaca cagcatc                                          27

<210> SEQ ID NO 10
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 10
ccccatcctg tgcgttggct gccg                                             24

<210> SEQ ID NO 11
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 11
ggagtcagct taagctgaat gggtctgc                                         28

<210> SEQ ID NO 12
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 12
ccggaattct ctacctccac catgcc                                           26

<210> SEQ ID NO 13
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 13
ccggaattcc tcagtgggca cacactcc                                         28
```

HYPOXIA INDUCING FACTORS AND USES THEREOF FOR INDUCING ANGIOGENESIS AND IMPROVING MUSCULAR FUNCTIONS

RELATED APPLICATIONS

This application is a Divisional Application of U.S. application Ser. No. 10/154,386, filed on May 23, 2002, now U.S. Pat. No. 7,608,698, which claims priority to U.S. Provisional Applications 60/292,630, filed May 23, 2001 and 60/354,529, filed Feb. 8, 2002, the disclosures of each of which are incorporated by reference herein in their entireties.

BACKGROUND OF THE INVENTION a) Field of the Invention

The present invention is concerned with a human protein called "HIF-3α" that is a Hypoxia Inducible Factor-3α and more particularly to the use of HIF-3α nucleic acids, proteins, fragments, antibodies, probes, and cells, to characterize HIF-3α, and modulate its cellular levels.

The present invention is also concerned with the use of nucleotide sequences encoding for proteins from the hypoxia inducible factors family for inducing VEGF expression, for inducing angiogenesis and for improving muscular functions, and more particularly, for treating coronary and cardiac diseases in mammals.

b) Brief Description of the Prior Art

Chronic ischemic heart disease is a worldwide health problem of major proportions. According to the American Heart Association, 61 800 000 Americans have at least one type of cardiovascular disease. In particular, coronary heart disease (CHD) cause myocardial infarction (MI) for 7 500 000 American patients and congestive heart failure (CHF) for 4 800 000 American patients. Almost 450 000 deaths in the United States alone were deemed to derive from CHD.

Current CHD treatments include medication, percutaneous transluminal coronary angioplasty and coronary artery bypass surgery. These procedures are quite successful to increase blood flow in the myocardium thus reducing ischemia and ameliorating the condition of the patient. However, due to the progressive nature of CHD, the beneficial effects of these procedures are not permanent and new obstructions can occur. Patients that live longer through effective cardiovascular interventions eventually run out of treatment options. Also an important patient population is still refractory to these treatments due to diffuse athereosclerotic diseases and/or small caliber arteries.

Severe and chronic ischemia can cause MI which is an irreversible scarring of the myocardium. This scarring reduces heart contractility and elasticity and consequently the pumping function, which can then lead to CHF. Treatments available to CHF patients target kidney function and peripheral vasculature to reduce the symptoms but none are treating the scar or increasing pump function of the heart. A very promising approach for reducing the scar and improving heart function is named cellular cardiomyoplasty (CCM). It consists in the injection of cells in the scar, replacing the fibrotic scar by healthy tissue and increasing elasticity (see U.S. Pat. No. 5,130,141; No. 5,602,301; No. 6,099,832 and No. 6,110,459).

Another emerging treatment for CHF patients is therapeutic angiogenesis. Angiogenesis is defined as blood vessel sprouting and proliferation from pre-existing vasculature. The net result is a higher capillary density and better blood perfusion. For instance, U.S. Pat. No. 5,792,453 disclose a method for promoting coronary collateral vessel development by delivering an adenovirus vector with a transgene encoding for an angiogenic protein. Although stimulation of angiogenesis can improve function of ischemic myocardium, it will have no effect on scar tissue because no viable cells will benefit from the improved perfusion.

Many growth factors are currently used to induce angiogenesis, including Vascular Endothelial Growth Factor (VEGF) and Fibroblast Growth Factor (FGF), but none of these factors has the property to stimulate every step of angiogenesis (basal membrane disruption, endothelial cell proliferation, migration and differentiation followed by periendothelial cells recruitment). Since it is known that cell hypoxia can naturally induce a strong angiogenesis, the use of regulators of hypoxia could stimulate the synthesis of one or many angiogenic factors at once, thereby resulting in a more structured and stronger angiogenesis than with individual factors.

Hypoxia Inducible Factors (HIFs) are heterodimeric transcription factors that regulate a number of adaptive responses to low oxygen tension. They are composed of alpha- and beta-subunits that belong to the basic helix-loop-helix-PAS (bHLH-PAS) superfamily. Members of this family include HIF-1α (also known as MOP1; see Wang et al., *Proc. Natl. Aca. Sci. USA* (1995) 92:5510-5514; and U.S. Pat. Nos. 5,882,314; 6,020,462 and 6,124,131), HIF-2α (also known as Endothelial PAS 1 (EPAS1), MOP2, HIF-related factor (HRF) and HLF (HIF-like factor), see Tian et al., *Genes & Dev.* (1996) 11:72-82; and U.S. Pat. No. 5,695,963).

Another member of the HIF family has been discovered recently, namely HIF-3α. The cloning of HIF-3α has been described in mice (Gu et al., *Gene Expression* (1998) 7:205-213; and in International PCT application WO 99/28264) and in rat (Kietzmann et al., *Biochem J.* (2001), 354 (Pt3):531-537). A partial cDNA sequence of human HIF-3α has been published in 1999 (GenBank™ accession No. AF079154), and a full length sequence of a human HIF-3α isoform, different from the one of the present invention, was published in October 2001 by Hara et al. (*Biochem. Biophys. Res. Comm.* (2001), October 5; 287:808-813).

HIFs are highly labile in normal conditions, but are stabilized in response to low oxygen tension. This stabilization allows them to bind to cis DNA elements of target genes, and stimulate transcription of hypoxia induced genes that help cell survival in low oxygen conditions. These target genes are implicated in processes such as anaerobic metabolism (glucose transporters and glycolytic enzymes), vasodilatation (inducible nitric oxide synthase (iNOS) and heme oxygenase-1 (HO-1)), increased breathing (tyrosine hydroxylase), erythropoiesis (erythropoietin) and angiogenesis (VEGF). Gene activation by HIF-1α or HIF-2α was demonstrated by co-transfection assays, in which a reporter gene is activated by the co-transfected HIF factor (Tian et al., *Genes & Dev.* (1996) 11: 72-82; Jiang et al., *J. Biol. Chem.* (1995) 272: 19253-19260). The role of HIF-2α in VEGF activation was also demonstrated in renal cell carcinoma (Xia et al., *Cancer* (2001), 91:1429-1436). In animal models, strong angiogenesis was reported following gene transfer of a hybrid HIF-1α/VP16 DNA construct (Vincent et al., *Circulation* (2000) 102: 2255-2261). However, prior to the present invention, it has never been demonstrated or suggested that HIF-2α or HIF-3α could induce the expression of angiogenesis-related gene(s) in mammalian muscular cells, nor that they could induce angiogenesis in these cells. It was also unknown that expression of HIF-1α, HIF-2α or HIF-3α in ischemic muscular tissue resulted in an increased metabolic activity of this tissue, indicating improved function.

Given that HIFs seem to represent ideal factors for VEGF activation and/or for induce angiogenesis, there is thus a need to identify a novel member of the HIF family. There is more particularly a need for a human HIF-3α protein and a nucleic acid encoding the same.

Also, it would be highly desirable to be provided with methods, compositions and cells for inducing angiogenesis and for improving muscular functions.

The present invention fulfils these needs and also other needs as it will be apparent to those skilled in the art upon reading the following specification.

SUMMARY OF THE INVENTION

The present inventors have discovered a novel member of the human Hypoxia Inducible Factors (HIFs) HIF-3α. The present inventors have also discovered uses for human HIF-3α proteins, fragments, nucleic acids, and antibodies for modulating HIF-3α cellular levels, for inducing VEGF expression in a mammalian cell, and for inducing angiogenesis in a mammalian tissue.

In general, the invention features an isolated or purified nucleic acid molecule, such as genomic, cDNA, antisense, DNA, RNA or a synthetic nucleic acid molecule that encodes or corresponds to a human HIF-3α polypeptide.

According to a first aspect, the invention features isolated or purified nucleic acid molecules, polynucleotides, polypeptides, human HIF-3α proteins and fragment thereof. Preferred nucleic acid molecules consist of a cDNA.

In a first embodiment, the isolated or purified nucleic acid molecule encodes a human protein that has the biological activity of a human HIF-3α polypeptide.

According to a specific embodiment, the nucleic acid of the invention comprises a sequence selected from the group consisting of:
a) sequences provided in SEQ ID NO: 1 or 3;
b) complements of the sequences provided in SEQ ID NO: 1 or 3;
c) sequences consisting of at least 20 contiguous residues of a sequence provided in SEQ ID NO: 1 or 3;
d) sequences that hybridize to a sequence provided in SEQ ID NO: 1 or 3, under moderately or strong stringent conditions;
e) sequences having at least 75% identity to a sequence of SEQ ID NO: 1 or 3; and
f) degenerate variants of a sequence provided in SEQ ID NO: 1 or 3.

More preferably, the nucleic acid molecule of the invention comprises a sequence selected from the group consisting of:
a) a nucleotide sequence having at least 75%, 80%, 85%, 90%, 95% or 97% nucleotide sequence identity with SEQ ID NO: 1; and
b) a nucleotide sequence having at least 75%, 80%, 85%, 90%, 95% or 97% nucleotide sequence identity with a nucleic acid encoding an amino acid sequence of SEQ ID NO:2.

Even more preferably, the nucleic acid molecule comprises a sequence substantially the same or having 100% identity with SEQ ID NO: 1 or a sequence substantially the same or having 100% identity with nucleic acids encoding an amino acid sequence of SEQ ID NO: 2. Most preferred nucleic acid molecules are those comprising part or all of nucleic acids 1423 to 1545 of SEQ ID NO: 1, and/or those comprising part or all of nucleic acids encoding a polypeptide with amino acids 475 to 515 of SEQ ID NO: 2.

According to another specific embodiment, the isolated or purified nucleic acid molecule comprises a sequence encoding a human HIF-3α polypeptide or degenerate variants thereof, the human HIF-3α polypeptide or degenerate variant comprising part or all of amino acids 475 to 515 of SEQ ID NO: 2. Preferably, the purified nucleic acid molecule comprises part or all of nucleic acids 1423 to 1545 of SEQ ID NO: 1. In an even more specific aspect, the invention features an isolated or purified human nucleic acid molecule comprising a polynucleotide having the SEQ ID NO: 1, or degenerate variants thereof, and encoding a human HIF-3α polypeptide. Preferably, the nucleic acid is a cDNA and it encodes the amino acid sequence of SEQ ID NO: 2 or a fragment thereof.

In a related aspect, the invention features an isolated or purified nucleic acid molecule which hybridizes under low, preferably moderate, and even more preferably high, stringency conditions to any of the nucleic acid molecules defined hereinbefore. More preferably, such nucleic acid molecules hybridizes under moderate or high stringency conditions with part or all of nucleic acids 1423 to 1545 of SEQ ID NO: 1, or with part or all of a complementary sequence thereof.

The invention also features substantially pure human polypeptides and proteins that are encoded by any of the above mentioned nucleic acids. In one embodiment, the protein has the biological activity of a human HIF-3α polypeptide. Preferred biological activity comprises induction of VEGF expression, thereby promoting angiogenesis.

In another embodiment, the invention aims at an isolated or purified polypeptide comprising an amino acid sequence selected from the group consisting of:
a) sequences having at least 80% identity to SEQ ID NO: 2;
b) sequences having at least 85% homology to SEQ ID NO: 2;
c) sequence provided in SEQ ID NO: 2;
d) sequences having at least 80% identity to amino acid sequences encoded by an open reading frame having SEQ ID NO: 3; and
e) sequences having at least 85% sequence homology to amino acid sequences encoded by an open reading frame having SEQ ID NO: 3.

More preferably, the polypeptide comprises an amino acid sequence selected from the group consisting of:
a) sequences substantially the same as SEQ ID NO: 2; and
b) sequences substantially the same as amino acid sequences encoded by an open reading frame having SEQ ID NO: 3.

In an even more specific aspect, the invention features a substantially pure human HIF-3α polypeptide or a fragment thereof, comprising part or all of amino acids 475 to 515 of SEQ ID NO: 2, or degenerate variants thereof. Even more preferably, the polypeptide comprises an amino acid sequence 100% identical to SEQ ID NO: 2.

The present invention also features protein fragments derived from any of the above mentioned protein or polypeptides. Similarly, the invention further encompasses polypeptides fragment comprising an amino acid sequence encoded by a nucleotide sequence comprising at least 24 sequential nucleic acids of SEQ ID NO:1 (hHIF-3α).

The present invention further features an antisense nucleic acid and a pharmaceutical composition comprising the same. Preferably, the antisense hybridizes under high stringency conditions to a genomic sequence or to a mRNA so that it reduces human HIF-3α cellular levels of expression. According to a first embodiment, the human HIF-3α polypeptide comprises amino acids 475 to 515 of SEQ ID NO: 2. More preferably, the human HIF-3α polypeptide is encoded by an open reading frame having SEQ ID NO: 3. According to a specific embodiment, the antisense hybridizes under high stringency condition with part or all of SEQ ID NO: 1, or with part or all of a complementary sequence thereof. More preferably, the antisense hybridizes under high stringency conditions with part or all of nucleic acids 1423 to 1545 of SEQ ID NO: 1, with part or all of nucleic acids 2116 to 2223 of SEQ ID NO: 1, or with part or all of complementary sequences thereof.

The present invention further relates to a pharmaceutical composition comprising: (1) at least one element selected from the group consisting of: (i) a nucleic acid molecule encoding a human HIF-3α polypeptide; (ii) a human HIF-3α polypeptide; (iii) an antisense nucleic acid that reduces a human HIF-3α polypeptide levels of expression; and (iv) an isolated or purified antibody that specifically binds to a HIF-3α polypeptide; and (2) a pharmaceutically acceptable carrier or diluent.

According to another aspect, the invention features a nucleotide probe comprising a sequence of at least 15, 20, 25, 30, 40, 50, 75 or 100 sequential nucleotides of SEQ ID NO: 1 or of a sequence complementary to SEQ ID NO:1. Preferably, the probe comprises part or all of nucleic acids 1423 to 1545 of SEQ ID NO: 1, part or all of nucleic acids 2116 to 2223 of SEQ ID NO: 1, part or all of nucleic acids encoding amino acids 475 to 515 of SEQ ID NO: 2, or part or all of a complementary sequence thereof. The invention also encompasses a substantially pure nucleic acid that hybridizes under low, preferably moderate, and more preferably under high stringency conditions to a probe of at least 20, 25, 30, 40, 50, 75 or 100 nucleotides in length that is derived from SEQ ID NO:1.

According to another aspect, the invention features a purified antibody. In a preferred embodiment, the antibody is a monoclonal or a polyclonal antibody that specifically binds to a purified mammalian HIF-3α polypeptide. Preferably, the antibody specifically binds to a HIF-3α polypeptide substantially the same as SEQ ID NO:2. More preferably, the antibody specifically binds to a HIF-3α polypeptide comprising part or all of amino acids 475 to 515 of SEQ ID NO:2 and even more preferably, the antibody specifically binds to part or all of amino acids 475 to 515 of SEQ ID NO:2.

In another aspect, the present invention further features a method for inducing VEGF expression in a mammalian cell. The method comprises introducing and expressing in the cell a nucleic acid sequence encoding polypeptide having the biological activity of a human HIF-3α polypeptide. In a preferred embodiment, the cell consists of a cardiac cell located in the heart of a living mammal, and expression of the polypeptide induces angiogenesis in cardiac tissue of the mammal. In another embodiment, the cell consists of a muscular cell located in muscular tissue of a living mammal, and expression of the polypeptide induces angiogenesis in the muscular tissue of the mammal. In another embodiment, the mammalian cell is a skeletal muscular cell thereby providing a HIF-3α expressing-skeletal muscular cell, and the method further comprises the step of transplanting a plurality of the HIF-3α expressing-skeletal muscular cells in a cardiac tissue of a compatible mammalian recipient.

Furthermore, the present invention features a method for inducing angiogenesis in a mammalian tissue having a plurality of cells, the method comprising the step of introducing and expressing in at least some of these cells a nucleic acid sequence encoding a polypeptide having the biological activity of a human HIF-3α polypeptide.

The present invention also features a method for modulating tumoral cell survival or for eliminating a tumoral cell in a mammal, comprising the step of reducing cellular expression levels of a HIF-3α polypeptide. According to a preferred embodiment, the mammal consists of a human, and a human HIF-3α antisense is introduced into the tumoral cell.

The present invention further features a method for determining the amount of a human HIF-3α polypeptide or a human HIF-3α nucleic acid in a biological sample, comprising the step of contacting the sample with an antibody or with a probe as defined previously.

According to a further aspect, the invention features a method of evaluating malignancy of a tumor in a human subject, comprising the step of measuring the amount of a HIF-3α polypeptide or of a HIF-3α nucleic acid in a tumoral cell from the subject, the amount being indicative of a degree of malignancy for the tumor.

In another related aspect, the invention features a kit for determining the amount of a HIF-3α polypeptide in a sample, the kit comprising an antibody or a probe as defined previously, and at least one element selected from the group consisting of instructions for using the kit, reaction buffer(s), and enzyme(s).

The nucleic acids of the invention may be incorporated into a vector and or a cell (such as a mammalian, yeast, nematode or bacterial cell). The nucleic acids may also be incorporated into a transgenic animal or embryo thereof. Therefore, the present invention features cloning or expression vectors, and hosts (such as transformed or transfected cells, transgenic animals) that contain any of the nucleic acids of the invention and more particularly those encoding a HIF-3α protein, polypeptide or fragment, and those capable of directing expression of a HIF-3α protein, polypeptide or fragment in a vector-containing cell.

In a related aspect, the invention features a method for producing a human HIF-3α polypeptide comprising:
  providing a cell transformed with a nucleic acid sequence encoding a human HIF-3α polypeptide positioned for expression in this cell;
  culturing the transformed cell under conditions suitable for expressing the nucleic acid; and
  producing the hHIF-3α polypeptide.

One of the greatest advantages of the present invention is that it provides nucleic acid molecules, proteins, polypeptides, antibodies, probes, and cells that can be used for characterizing HIF-3α, modulate its cellular levels, and promotes angiogenesis.

Other objects and advantages of the present invention will be apparent upon reading the following non-restrictive description of the preferred embodiments thereof and from the claims.

DETAILED DESCRIPTION OF THE INVENTION

A) Definitions

Figure 1:
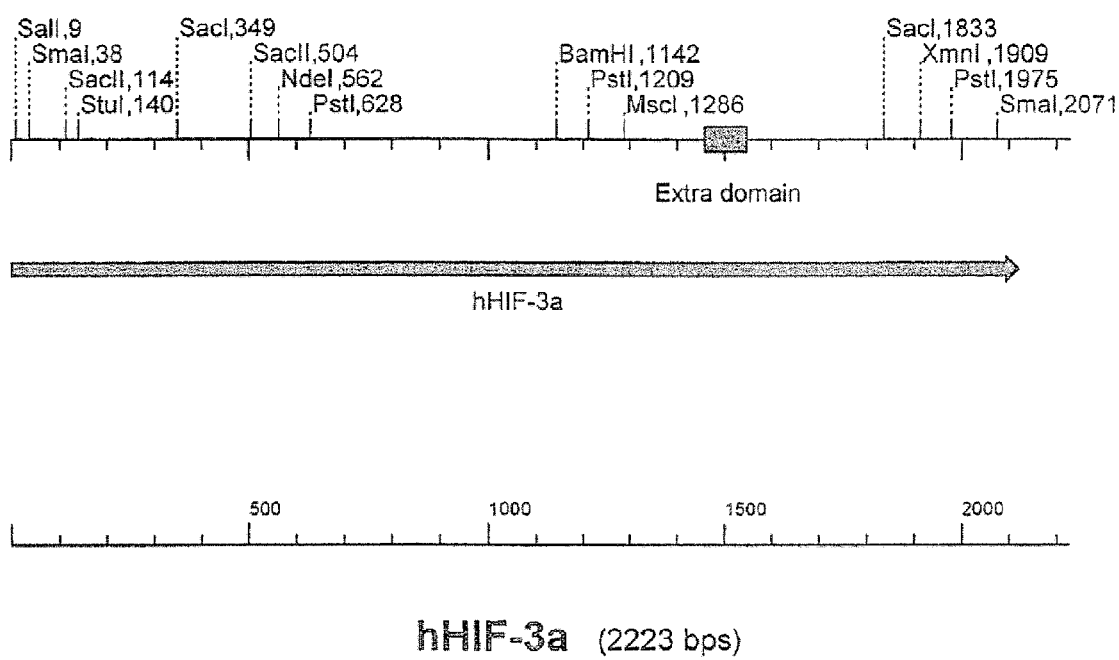
FIG. 1 is a schema illustrating the human HIF-3α gene organization.

Throughout the text, the word "kilobase" is generally abbreviated as "kb", the words "deoxyribonucleic acid" as "DNA", the words "ribonucleic acid" as "RNA", the words "complementary DNA" as "cDNA", the words "polymerase chain reaction" as "PCR", and the words "reverse transcription" as "RT". Nucleotide sequences are written in the 5' to 3' orientation unless stated otherwise.

In order to provide an even clearer and more consistent understanding of the specification and the claims, including the scope given herein to such terms, the following definitions are provided:

Antisense: as used herein in reference to nucleic acids, is meant a nucleic acid sequence, regardless of length, that is complementary to the coding strand of a gene.

Expression: refers to the process by which gene encoded information is converted into the structures present and operating in the cell. In the case of cDNAs, cDNA fragments and genomic DNA fragments, the transcribed nucleic acid is subsequently translated into a peptide or a protein in order to carry out its function if any. By "positioned for expression" is meant that the DNA molecule is positioned adjacent to a DNA sequence which directs transcription and translation of the sequence (i.e., facilitates the production of, e.g., a HIF-3α polypeptide, a recombinant protein or a RNA molecule).

Fragment: Refers to a section of a molecule, such as a protein, a polypeptide or a nucleic acid, and is meant to refer to any portion of the amino acid or nucleotide sequence.

Host: A cell, tissue, organ or organism capable of providing cellular components for allowing the expression of an exogenous nucleic acid embedded into a vector or a viral genome, and for allowing the production of viral particles encoded by such vector or viral genome. This term is intended to also include hosts which have been modified in order to accomplish these functions. Bacteria, fungi, animal (cells, tissues, or organisms) and plant (cells, tissues, or organisms) are examples of a host.

Isolated or Purified or Substantially pure: Means altered "by the hand of man" from its natural state, i.e., if it occurs in nature, it has been changed or removed from its original environment, or both. For example, a polynucleotide or a protein/peptide naturally present in a living organism is not "isolated", the same polynucleotide separated from the coexisting materials of its natural state, obtained by cloning, amplification and/or chemical synthesis is "isolated" as the term is employed herein. Moreover, a polynucleotide or a protein/peptide that is introduced into an organism by transformation, genetic manipulation or by any other recombinant method is "isolated" even if it is still present in said organism.

Nucleic acid: Any DNA, RNA sequence or molecule having one nucleotide or more, including nucleotide sequences encoding a complete gene. The term is intended to encompass all nucleic acids whether occurring naturally or non-naturally in a particular cell, tissue or organism. This includes DNA and fragments thereof, RNA and fragments thereof, cDNAs and fragments thereof, expressed sequence tags, artificial sequences including randomized artificial sequences.

Open reading frame ("ORF"): The portion of a cDNA that is translated into a protein. Typically, an open reading frame starts with an initiator ATG codon and ends with a termination codon (TAA, TAG or TGA).

Polypeptide: means any chain of more than two amino acids, regardless of post-translational modification such as glycosylation or phosphorylation.

Percent identity and Percent similarity: used herein in comparisons or nucleic acid and/or among amino acid sequences. Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Owl 53705). This software program matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

HIF-3α nucleic acid: means any nucleic acid (see above) encoding a mammalian polypeptide that has the biological activity of activating, in an hypoxia inducible fashion, target genes such as VEGF and having at least 75%, 77%, 80%, 85%, 90%, 95%, 97% or 100% identity or homology to the amino acid sequence shown in SEQ. ID. NO: 2. Even more preferably, the mammalian HIF-3α polypeptide comprises amino acids having at least 75%, 77%, 80%, 85%, 90%, 95%, 97% or 100% identity or homology to amino acids 475 to 515 of SEQ ID NO: 2. When referring to a human HIF-3α nucleic acid, the nucleic acid encoding SEQ. ID. NO: 2 is more particularly concerned. HIF-3α protein or HIF-3α polypeptide: means a protein, a polypeptide, or a fragment thereof, encoded by a HIF3α nucleic acid as described above.

Specifically binds: means an antibody that recognizes and binds a protein or polypeptide but that does not substantially recognize and bind other molecules in a sample, e.g., a biological sample, that naturally includes protein.

Substantially the same: refers to nucleic acid or amino acid sequences having sequence variation that do not materially affect the nature of the protein. With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function of the protein.

Substantially pure polypeptide: means a polypeptide that has been separated from the components that naturally accompany it. Typically, the polypeptide is substantially pure when it is at least 60%, by weight, free from the proteins and naturally-occurring organic molecules with which it is naturally associated. Preferably, the polypeptide is a HIF-3α polypeptide that is at least 75%, 80%, or 85%, more preferably at least 90%, 95% or 97% and most preferably at least 99%, by weight, pure. A substantially pure HIF-3α polypeptide may be obtained, for example, by extraction from a natural source (including but not limited to lung cells, kidney cells, heart cells or any other cell expressing HIF-3α) by expression of a recombinant nucleic acid encoding a HIF-3α polypeptide, or by chemically synthesizing the protein. Purity can be measured by any appropriate method, e.g., by column chromatography, polyacrylamide gel electrophoresis, or HPLC analysis. A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in E. coli or other prokaryotes. By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding an additional polypeptide sequence.

Transformed or Transfected or Transduced or Transgenic cell: refers to a cell into which (or into an ancestor of which) has been introduced, by means of recombinant DNA techniques, a DNA molecule encoding (as used herein) a HIF-3α polypeptide. By "transformation" is meant any method for introducing foreign molecules into a cell. Lipofection, calcium phosphate precipitation, retroviral delivery, electroporation, and ballistic transformation are just a few of the teachings which may be used.

Transgenic animal: any animal having a cell which includes a DNA sequence which has been inserted by artifice into the cell and becomes part of the genome of the animal which develops from that cell. As used herein, the transgenic animals are usually mammalian (e.g., rodents such as rats or mice) and the DNA (transgene) is inserted by artifice into the nuclear genome.

Vector: A self-replicating RNA or DNA molecule which can be used to transfer an RNA or DNA segment from one organism to another. Vectors are particularly useful for manipulating genetic constructs and different vectors may have properties particularly appropriate to express protein(s) in a recipient during cloning procedures and may comprise different selectable markers. Bacterial plasmids are commonly used vectors. Modified viruses such as adenoviruses and retroviruses are other examples of vectors.

B) General Overview of the Invention

The invention generally concerns a protein novel member of the Hypoxia inducible factors (HIFs) HIF-3α. The present inventors have also discovered uses for human HIF-3α proteins, fragments, nucleic acids, and antibodies for modulating HIF-3α cellular levels, for inducing VEGF expression in a mammalian cell, and for inducing angiogenesis in a mammalian tissue. This aspect of the invention also concerns the uses of human HIF-3α proteins, fragments, nucleic acids, and antibodies for modulating HIF-3α cellular levels and for the treatment of coronary and cardiac diseases in mammals, including humans.

The invention also concerns methods and cells, and more particularly genetically modified muscular cells expressing a plurality of angiogenesis-related genes, for inducing angiogenesis and for improving muscular functions. This additional aspect of the invention is based on the use of a nucleotide sequence encoding a transcription factor from the hypoxia inducible factors family (HIF-1α, HIF-2α, and HIF-3α) and provides numerous advantages in the treatment of coronary and cardiac diseases in mammals, including humans.

i) Cloning and Molecular Characterization of HIF-3α

As it will be described hereinafter in the exemplification section of the invention, the inventors have discovered, cloned and sequenced a human cDNA encoding a new human protein member from the Hypoxia Inducible Factor family, called human HIF-3α (hHIF-3α).

The sequence of the HIF-3α cDNA and predicted amino acid sequence is shown in the "Sequence Listing" section. SEQ ID NO: 1 corresponds to the human HIF-3α cDNA and SEQ ID NO: 2 corresponds to the predicted amino acid sequence of the human protein. SEQ ID NO: 3 corresponds to HIF-3α Open reading frame.

The HIF-3α gene encodes a protein of 705 amino acids (A.A.) long. In silico analysis indicates that human HIF-3α protein has the following features: it has a molecular weight of about 76 kDa, an isoelectric point of about 5.95; an instability index of about 55.6 (i.e. unstable); an aliphatic index of about 80.6; and a grand average of hydropathicity (GRAVY) of about 0.388. It further comprises many potential phosphorylation sites (45 Ser, 12 Thr, and 3 Tyr) and also many potential phosphorylation sites. Predicted protein domains include the Helix Loop Helix (HLH) heterodimerization domain encoded by amino acids 14-62. This domain is characteristic of HLH transcription factor family. Then, 2 PAS (A.A. 84-143 and 235-289) and 1 PAC (A.A. 295-337) domains are identified, these domains are all common to the PAS family (a sub-family to the HLH factors).

ii) HIF-3α Homologoy with Other Genes and Proteins

The cloning of hHIF-3α was carried out starting with the mouse HIF-3α sequence.

A blast search was made to identify sequence identity between hHIF-3α of the present invention, mHIF-3α and other existing sequences (see Table 1 hereinbelow). It was found that further to mice (GenBank™ accession No. AF060194), HIF-3α had also been sequenced in rat (GenBank™ accession No. NM_022528).

Furthermore, the present inventors also found that their hHIF-3α sequence also shared high level of identity with another, recently cloned hHIF-3α sequence (GenBank™ accession No. AB054067) published by Hara et al. (*Biochem. Biophys. Res. Comm.* (2001), October 5; 287:808-813). This sequence was published subsequent to the filing date of the application on which the present application claims the benefit. The Hara et al. hHIF-3α sequence seems to be another isoform of HIF-3α, that differs from the hHIF-3α according to the present invention since it is depleted from nucleic acids 1423 to 1545 of SEQ ID NO:1 encoding amino acids 475 to 515 of SEQ ID NO:2. Equivalent mouse and rat sequences also lack amino acids homologues to 475-515 amino acids 475 to 515 of SEQ ID NO:2 and are thus homologues of Hara et al. hHIF-3α sequence. Although not shown, nucleic acids 7 to 345 of SEQ ID NO:1 also shares 100% identity with nucleotides 7 to 345 of a partial cDNA sequence of human HIF-3α published in 1999 (GenBank™ accession No. AF079154), this sequence encoding a 115 amino acid residues (GenBank™ accession No. AAC99397), the last 113 amino acids sharing 100% identity with amino acids 3 to 115 of SEQ ID NO:2.

TABLE 1

Identified isoform Sequence identity and homology of human HIF-3α (SEQ ID NOs 1 and 2) to known sequence

| Gene | cDNA identity[1] | Amino acid identity | Amino acid similarity |
|---|---|---|---|
| Human HIF-3α[2] | 89% | 93% | 93% |
| Mouse HIF-3α[3] | 74% | 77% | 82% |
| Rat HIF-3α[4] | 73% | 75% | 80% |

[1]Alignment limited to coding sequence and excluding untranslated regions.
[2]GenBank access AB054067
[3]GenBank access AF060194
[4]GenBank access NM_022528

Therefore, the present invention concerns an isolated or purified nucleic acid molecule (such as cDNA) comprising a sequence selected from the group consisting of:
a) sequences provided in SEQ ID NO: 1 or 3;
b) complements of the sequences provided in SEQ ID NO: 1 or 3;
c) sequences consisting of at least 20 contiguous residues of a sequence provided in SEQ ID NO: 1 or 3;
d) sequences that hybridize to a sequence provided in SEQ ID NO: 1 or 3, under moderately or strong stringent conditions;
e) sequences having at least 75% identity to a sequence of SEQ ID NO: 1 or 3; and
f) degenerate variants of a sequence provided in SEQ ID NO: 1 or 3.

More preferably, the nucleic acid molecule of the invention comprises a sequence selected from the group consisting of:
a) a nucleotide sequence having at least 75%, 80%, 85%, 90%, 95% or 97% nucleotide sequence identity with SEQ ID NO: 1; and
b) a nucleotide sequence having at least 75%, 80%, 85%, 90%, 95% or 97% nucleotide sequence identity with a nucleic acid encoding an amino acid sequence of SEQ ID NO:2.

More preferably, the nucleic acid molecule comprises a sequence substantially the same or having 100% identity with SEQ ID NO: 1 or a sequence substantially the same or having 100% identity with nucleic acids encoding an amino acid sequence of SEQ ID NO: 2. Most preferred nucleic acid molecules are those comprising part or all of nucleic acids 1423 to 1545 of SEQ ID NO: 1, and/or those comprising part or all of nucleic acids encoding a polypeptide with amino acids 475 to 515 of SEQ ID NO: 2.

The present invention also concerns isolated or purified nucleic acid molecules comprising a sequence encoding a human HIF-3α polypeptide or degenerate variants thereof (the human HIF-3α polypeptide or degenerate variant comprising part or all of amino acids 475 to 515 of SEQ ID NO: 2) and purified nucleic acid molecules comprising part or all of nucleic acids 1423 to 1545 of SEQ ID NO: 1.

The present invention also concerns isolated or purified nucleic acid molecule which hybridizes under moderate, preferably high stringency conditions with part or all of any of the HIF-3α nucleic acid molecules of the invention mentioned hereinbefore or with part or all of a complementary sequence thereof. More preferably, the "hybridizing" nucleic acid hybridizes under moderate, preferably high stringency conditions with part or all of nucleic acids 1423 to 1545 of SEQ ID NO: 1, or with part or all of a complementary sequence thereof. The "hybridizing" nucleic acid could be used as probe or as antisense molecules as it will be described hereinafter.

In a related aspect, the present invention concerns an isolated or purified polypeptide, comprising an amino acid sequence selected from the group consisting of:
a) sequences encoded by part or all of the HIF-3α nucleic acid molecules of the invention mentioned hereinbefore;
b) sequences having at least 80% identity to SEQ ID NO: 2;
c) sequences having at least 85% homology to SEQ ID NO: 2;
d) sequence provided in SEQ ID NO: 2;
e) sequences having at least 80% identity to amino acid sequences encoded by an open reading frame having SEQ ID NO: 3; and
f) sequences having at least 85% sequence homology to amino acid sequences encoded by an open reading frame having SEQ ID NO: 3.

More preferably, the polypeptide comprises an amino acid sequence substantially the same or having 100% identity with SEQ ID NO: 2 or a sequence substantially the same or having 100% identity with amino acid sequences encoded by an open reading frame having SEQ ID NO: 3. Event more preferably, the polypeptides comprise part or all of amino acids 475 to 515 of SEQ ID NO: 2, or degenerate variants thereof, or comprise part or all of amino acids encoded by nucleic acids 1423 to 1545 of SEQ ID NO: 1. Most preferred polypeptides are those having the biological activity of a human HIF-3α polypeptide, such as VEGF expression inducement capabilities for the promotion of angiogenesis.

iii) Vectors, Cells and Transgenic Animals

The invention is also directed to a host, such as a genetically modified cell, expressing a functional HIF-3α transcription factor. Preferably, the cell is a skeletal muscular cell or a cardiac cell. Preferably also, the cell comprises a cDNA encoding the transcription factor.

The HIF-3α expressing cell may be a transiently-transfected mammalian cell line (such as HEK293 cells, a Hep3B cells, and the like) or any suitable isolated primary cells, including by not limited to mammalian skeletal muscular cells, cardiac cells, bone marrow cells, fibroblasts, smooth muscle cells, endothelial cells, endothelial progenitor cells and embryonic stem cells A number of vectors suitable for stable transfection of mammalian cells are available to the public (e.g. plasmids, adenoviruses, adeno-associated viruses, retroviruses, Herpes Simplex Viruses, Alphaviruses, Lentiviruses), as are methods for constructing such cell lines. The present invention encompasses any type of vector with a HIF-3α sequence.

The cells of the invention may be particularly useful when transplanted in a compatible recipient for inducing angiogenesis, relieving ischemia, increasing the metabolic activity of a mammalian muscular tissue, and/or increasing muscular function in CHF or in peripheral vascular disease, locally or in surrounding transplanted tissue. Of course, the genetically modified cells of the present invention could also be used for the formation of artificial organs or for tissue constructions. HIF-3α expressing cells may also be used for producing HIF-3α and derivatives thereof (see hereinafter).

The mammalian HIF-3α according to the present invention or a fragment thereof may also be used to generate 1) transgenic animals that express the HIF-3α gene or HIF-3α mutants at various levels in one or multiple cell lineages, 2) knock-out animal in which expression of the endogenous HIF-3α gene is either prevented or regulated in one or multiple cell lineages.

Characterization of HIF-3α genes provides information that is necessary for a HIF-3α knockout animal model to be developed by homologous recombination. Preferably, the model is a mammalian animal, most preferably a mouse. Similarly, an animal model of HIF-3α overproduction may be generated by integrating one or more HIF-3α sequences into the genome, according to standard transgenic techniques.

iv) Synthesis of HIF-3α and Functional Derivative Thereof

Knowledge of human HIF-3α gene sequence open the door to a series of applications. For instance, the characteristics of the cloned HIF-3α gene sequence may be analyzed by introducing the sequence into various cell types or using in vitro extracellular systems. The function of HIF-3α may then be examined under different physiological conditions. The HIF-3α cDNA sequence may be manipulated in studies to understand the expression of the gene and gene product. Alternatively, cell lines may be produced which overexpress the gene product allowing purification of HIF-3α for biochemical characterization, large-scale production, antibody production, and patient therapy.

For protein expression, eukaryotic and prokaryotic expression systems may be generated in which the HIF-3α gene sequence is introduced into a plasmid or other vector which is then introduced into living cells. Constructs in which the HIF-3α cDNA sequence containing the entire open reading frame inserted in the correct orientation into an expression plasmid may be used for protein expression. Alternatively, portions of the sequence, including wild-type or mutant HIF-3α sequences, may be inserted. Prokaryotic and eukaryotic expression systems allow various important functional domains of the protein to be recovered as fusion proteins and then used for binding, structural and functional studies and also for the generation of appropriate antibodies.

Eukaryotic expression systems permit appropriate post-translational modifications to expressed proteins. This allows for studies of the HIF-3α gene and gene product including determination of proper expression and post-translational modifications for biological activity, identifying regulatory elements located in the 5' region of the HIF-3α gene and their role in tissue regulation of protein expression. It also permits the production of large amounts of normal and mutant proteins for isolation and purification, to use cells expressing HIF-3α as a functional assay system for antibodies generated against the protein, to test the effectiveness of pharmacological agents or as a component of a signal transduction system, to study the function of the normal complete protein, specific portions of the protein, or of naturally occurring polymorphisms and artificially produced mutated proteins. The HIF-3α DNA sequence may be altered by using procedures such as restriction enzyme digestion, DNA polymerase fill-in, exonuclease deletion, terminal deoxynucleotide transferase extension, ligation of synthetic or cloned DNA sequences and site directed sequence alteration using specific oligonucleotides together with PCR.

Accordingly, the invention also concerns a method for producing a human a human HIF-3α polypeptide. The method comprises the steps of: (i) providing a cell transformed with a nucleic acid sequence encoding a human HIF-3α polypeptide positioned for expression in the cell; (ii) culturing the transformed cell under conditions suitable for expressing the nucleic acid; (iii) producing said a human HIF-3α polypeptide; and optionally, (iv) recovering the human HIF-3α polypeptide produced.

Once the recombinant protein is expressed, it is isolated by, for example, affinity chromatography. In one example, an anti-HIF-3α antibody, which may be produced by the methods described herein, can be attached to a column and used to isolate the HIF-3α protein. Lysis and fractionation of HIF-3α-harboring cells prior to affinity chromatography may be performed by standard methods. Once isolated, the recombinant protein can, if desired, be purified further.

Methods and techniques for expressing recombinant proteins and foreign sequences in prokaryotes and eukaryotes are well known in the art and will not be described in more detail. One can refer, if necessary to Joseph Sambrook, David W. Russell, Joe Sambrook Molecular Cloning: A Laboratory Manual 2001 Cold Spring Harbor Laboratory Press. Those skilled in the art of molecular biology will understand that a wide variety of expression systems may be used to produce the recombinant protein. The precise host cell used is not critical to the invention. The HIF-3α protein may be produced in a prokaryotic host (e.g., *E. coli* or in a eukaryotic host (e.g., *S. cerevisiae*, insect cells such as Sf21 cells, or mammalian cells such as COS-1, NIH 3T3, or HeLa cells). These cells are publicly available, for example, from the American Type Culture Collection, Rockville, Md. The method of transduction and the choice of expression vehicle will depend on the host system selected.

Polypeptides of the invention, particularly short HIF-3α fragments, may also be produced by chemical synthesis. These general techniques of polypeptide expression and purification can also be used to produce and isolate useful HIF-3α fragments or analogs, as described herein.

Skilled artisans will recognize that a mammalian HIF-3α, or a fragment thereof (as described herein), may serve as an active ingredient in a therapeutic composition. This composition, depending on the HIF-3α or fragment included, may be used to regulate cell proliferation, survival and angiogenesis and thereby treat any condition that is caused by a disturbance in cell proliferation, accumulation or replacement. Thus, it will be understood that another aspect of the invention described herein, includes the compounds of the invention in a pharmaceutically acceptable carrier.

v) Uregulation of HIF-3α Expression for Promoting Angiogenesis

Knowledge of human HIF-3α gene sequence provides novel promising approaches for patient therapy. As it will be shown in details hereinafter in the exemplification section of the application, upregulation of HIF-3α expression could be used to increase VEGF expression in mammalian cells and thereby promote angiogenesis in ischemic and non-ischemic tissue of mammals, preferably animal models and humans.

Therefore, the invention also relates to methods for inducing VEGF expression in a mammalian cell by introducing and expressing in the cell a nucleic acid sequence encoding polypeptide having the biological activity of a human HIF-3α polypeptide. Of course, other nucleic acids, such as those which expression is known to also induce VEGF expression, may be introduced and expressed in the cell together with HIF-3α.

Another related aspect of the invention concerns methods for inducing angiogenesis in a mammalian tissue having a plurality of cells, by introducing and expressing in at least some of these cells a nucleic acid sequence encoding a polypeptide having the biological activity of a human HIF-3α polypeptide.

Preferably, these methods are achieved by transfecting in vitro, in vivo or ex vivo cells with a HIF-3α cDNA, the human HIF-3α polypeptide comprises an amino acid sequence substantially the same as SEQ ID NO:2.

As mentioned previously in the "background" section, stimulation of angiogenesis may be beneficial for the treatment of coronary heart diseases. Therefore, the human HIF-3α sequence of the invention could be advantageously used for such purposes. In one embodiment, the cell consists of a cardiac cell located in the heart of a living mammal, and the HIF-3α nucleic acid sequence is introduced in a plurality of these cardiac cell such that expression of the HIF-3α polypeptide induce angiogenesis in cardiac tissue of the mammal. Introduction of the HIF-3α nucleic acid sequence may be done by using a vector as defined previously or by any suitable technique known in the art.

In another embodiment, the cell consists of an isolated muscular cell (preferably skeletal muscular cell), and this cell is genetically modified so as to express the HIF-3α polypeptide. Genetically modified HIF-3α expressing cells are then transplanted in tissue (e.g. cardiac tissue) of a compatible mammalian recipient. More preferably, the transplantation is autologous (the cells are isolated from muscular tissue, such as leg, of the recipient), and the cells are transplanted to the recipient (such as an injection in the scar of the heart) in an amount that is sufficient to induce angiogenesis locally or in surrounding transplanted tissue.

In yet another embodiment, the cell consists of a muscular cell located in muscular tissue of a living mammal, and expression of the HIF-3α polypeptide induce angiogenesis in the muscular tissue of the mammal (autologous or heterologous transplantation). This method is particularly useful for treating peripheral artery diseases (e.g. ischemia in the legs due to femoral or upstream artery obstruction in humans).

The nucleotide sequence may be introduced in the cell or tissue using well known methods. Indeed, the sequence(s) may be introduced directly in the cells of a given tissue, injected in the tissue, or introduced via the transplantation of previously genetically modified compatible cells (see hereinafter). Methods for introducing a nucleotide sequence into eukaryote cells such as mammalian muscular cells or for genetically modifying such cells are well known in the art. For instance, this may be achieved with adenoviral vectors, plasmid DNA transfer (naked DNA or complexed with liposomes) or electroporation. If necessary, a person skilled in the art may look at Isner J., (*Nature* (2002), 415:234-239) for a review of myocardial gene therapy methods and to US patent application US20010041679A1 or U.S. Pat. No. 5,792,453 which provides methods of gene transfer-mediated angiogenesis therapy. Preferably, the level of expression of the transcription factor(s) is such that the angiogenesis-related gene is expressed at a level that is sufficient to induce angiogenesis locally or in surrounding tissue. For better controlling its expression and selectivity, the transcription factor may be inducible.

In preferred embodiments, a plurality of genetically modified skeletal muscular cells are transplanted into the heart of a compatible recipient. Preferably, the transplantation is autologous. More preferably, the cells are transplanted in an amount that is sufficient to induce angiogenesis locally or in surrounding transplanted tissue. Even more preferably, the transplantation improves the recipient's cardiac functions. Transplantation methods, are well known in the art. For detailed examples of muscular cell transplantation, one may refer to U.S. Pat. Nos. 5,602,301 and 6,099,832.

vi) Downregulation of HIF-3α Expression

As mentioned previously, HIF-3α expression induces VEGF expression, which itself promotes angiogenesis. Since it is well known that tumoral cell survival depend on angiogenesis, we propose that, in some tumors, HIF-3α expression is essential for cancer cell proliferation. Accordingly, downmodulation of HIF-3α could be used to prevent and/or treat these tumors.

Therefore, the invention relates to methods for modulating tumoral cell survival or for eliminating a tumoral cell in a human by reducing cellular expression levels of a human HIF-3α polypeptide. In a preferred embodiment, this is achieved by delivering an antisense into the tumoral cells. This can be achieved by intravenous injection, intratumoral injection or other local drug delivery using currently available methods (e.g. Crooke et al., (2000), *Oncogene* 19, 6651-6659; Stein et al. (2001), *J. Clin. Invest* 108, 641-644; and Tamm et al., (2001), *Lancet* 358, 489-497).

According to a related aspect of the above-mentioned method, the invention relates to antisense nucleic acids and to pharmaceutical compositions comprising such antisenses, the antisense being capable of reducing HIF-3α cellular levels of expression, and more particularly the level of expression of human HIF-3α polypeptide encoded by an open reading frame having SEQ ID NO: 3 and/or comprising amino acids 475 to 515 of SEQ ID NO: 2. Preferably, the antisense nucleic acid is complementary to a nucleic acid sequence encoding a hHIF-3α protein or encoding any of the polypeptides derived therefrom. More preferably, the antisense hybridizes under high stringency conditions to a genomic sequence or to a mRNA, even more preferably under high stringency conditions with part or all of SEQ ID NO: 1, or with part or all of a complementary sequence thereof. Most preferred antisense molecules are those which hybridize under high stringency conditions with part or all of nucleic acids 1423 to 1545 of SEQ ID NO:1, with part or all of nucleic acids 2116 to 2223 of SEQ ID NO:1, or with part or all of complementary sequences thereof.

A non-limitative example of high stringency conditions includes:
  a) pre-hybridization and hybridization at 68° C. in a solution of 5×SSPE (1×SSPE=0.18 M NaCl, 10 mM NaH$_2$PO$_4$); 5×Denhardt solution; 0.05% (w/v) sodium dodecyl sulfate (SDS); et 100 µg/ml salmon sperm DNA;
  b) two washings for 10 min at room temperature with 2×SSPE and 0.1% SDS;
  c) one washing at 60° C. for 15 min with 1×SSPE and 0.1% SDS; and
  d) one washing at 60° C. for 15 min with 0.1×SSPE et 0.1% SDS.

vii) HIF-3α Antibodies

The invention features purified antibodies that specifically binds to a HIF-3α protein. The antibodies of the invention may be prepared by a variety of methods using the HIF-3α proteins or polypeptides described above. For example, the HIF-3α polypeptide, or antigenic fragments thereof, may be administered to an animal in order to induce the production of polyclonal antibodies. Alternatively, antibodies used as described herein may be monoclonal antibodies, which are prepared using hybridoma technology (see, e.g., Hammerling et al., In Monoclonal Antibodies and T-Cell Hybridomas, Elsevier, N.Y., 1981). The invention features antibodies that specifically bind human HIF-3α polypeptides, or fragments thereof. In particular, the invention features "neutralizing" antibodies. By "neutralizing" antibodies is meant antibodies that interfere with any of the biological activities of the HIF-3α polypeptide, particularly the ability of HIF-3α to induce VEGF expression. The neutralizing antibody may reduce the ability of HIF-3α polypeptides to inhibit VEGF expression by, preferably 50%, more preferably by 70%, and most preferably by 90% or more. Any standard assay of VEGF expression, including those described herein, may be used to assess potentially neutralizing antibodies. Once produced, monoclonal and polyclonal antibodies are preferably tested for specific HIF-3α recognition by Western blot, immunoprecipitation analysis or any other suitable method.

In addition to intact monoclonal and polyclonal anti-HIF-3α antibodies, the invention features various genetically engineered antibodies, humanized antibodies, and antibody fragments, including F(ab')2, Fab', Fab, Fv and sFv fragments. Antibodies can be humanized by methods known in the art. Fully human antibodies, such as those expressed in transgenic animals, are also features of the invention.

Antibodies that specifically recognize HIF-3α (or fragments of HIF-3α), such as those described herein, are considered useful to the invention. Such an antibody may be used in any standard immunodetection method for the detection, quantification, and purification of a HIF-3α polypeptide. Preferably, the antibody binds specifically to HIF-3α. The antibody may be a monoclonal or a polyclonal antibody and may be modified for diagnostic or for therapeutic purposes. More preferably the antibody specifically binds the a HIF-3α polypeptide comprising part or all of amino acids 475 to 515 of SEQ ID NO:2. The most preferred antibodies are those that specifically binds to part or all of amino acids 475 to 515 of SEQ ID NO:2.

The antibodies of the invention may, for example, be used in an immunoassay to monitor HIF-3α expression levels, to determine the subcellular location of a HIF-3α or HIF-3α fragment produced by a mammal or to determine the amount of HIF-3α or fragment thereof in a biological sample. Antibodies that inhibit HIF-3α described herein may be especially useful for conditions where decreased HIF-3α function would be advantageous such as inhibition of cancer cell proliferation (see hereinafter). In addition, the antibodies may be coupled to compounds for diagnostic and/or therapeutic uses such as radionucleotides for imaging and therapy and liposomes for the targeting of compounds to a specific tissue location. The antibodies may also be labeled (e.g. immunofluorescence) for easier detection.

viii) Administration of HIF-3α Polypeptides, Modulators of HIF-3α Synthesis or Function Therapies may be designed to circumvent or overcome an inadequate HIF-3α gene expression. This could be accomplished for instance by transfection of HIF-3α cDNA.

To obtain large amounts of pure HIF-3α, cultured cell systems would be preferred. Delivery of the protein to the affected tissues can then be accomplished using appropriate packaging or administrating systems. Alternatively, it is conceivable that small molecule analogs could be used and administered to act as HIF-3α agonists and in this manner produce a desired physiological effect. Methods for finding such molecules are provided herein.

A HIF-3α protein or polypeptide, polypeptide, antibody or modulator (e.g. antisense) may be administered within a pharmaceutically acceptable diluent, carrier, or excipient, in unit dosage form. Conventional pharmaceutical practice may be used to provide suitable formulations or compositions to administer HIF-3α protein, polypeptide, or modulator to patients. Administration may begin before the patient is symptomatic. Any appropriate route of administration may be employed, for example, administration may be parenteral, intravenous, intraarterial, subcutaneous, intramuscular, intracranial, intraorbital, ophthalmic, intraventricular, intracapsular, intraspinal, intracisternal, intraperitoneal, intranasal, aerosol, by suppositories, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with a HIF-3α protein, polypeptide, or modulatory compound may be combined with more traditional therapies for the disease such as surgery, steroid therapy, or chemotherapy.

According to a preferred embodiment, a HIF-3α antisense would be incorporated in a pharmaceutical composition comprising at least one of the oligonucleotides defined previously, and a pharmaceutically acceptable carrier. The amount of antisense present in the composition of the present invention is a therapeutically effective amount. A therapeutically effective amount of antisense is that amount necessary so that the antisense performs its biological function without causing overly negative effects in the host to which the composition is administered. The exact amount of oligonucleotides to be used and composition to be administered will vary according to factors such as the oligo biological activity, the type of condition being treated, the mode of administration, as well as the other ingredients in the composition. Typically, the composition will be composed of about 1% to about 90% of antisense, and about 20 µg to about 20 mg of antisense will be administered. For preparing and administering antisenses as well as pharmaceutical compositions comprising the same, methods well known in the art may be used. For instance, see Crooke et al. (*Oncogene*, 2000, 19:6651-6659) and Tamm et al. (*Lancet* 200, 1358:489-497) for a review of antisense technology in cancer chemotherapy.

ix) Assessment of HIF-3α Intracellular or Extracellular Levels

As noted, the antibodies and probes described above may be used to monitor HIF-3α protein expression and/or to determine the amount of HIF-3α or fragment thereof in a biological sample, and/or to evaluate malignancy of a tumor in a human subject.

In addition, in situ hybridization may be used to detect the expression of the HIF-3α gene. As it is well known in the art, in situ hybridization relies upon the hybridization of a specifically labeled nucleic acid probe to the cellular RNA in individual cells or tissues. Therefore, oligonucleotides or cloned nucleotide (RNA or DNA) fragments corresponding to unique portions of the HIF-3α gene may be used to assess HIF-3α cellular levels or detect specific mRNA species. Such an assessment may also be done in vitro using well known methods (Northern analysis, quantitative PCR, etc.).

Determination of the amount of HIF-3α or fragment thereof in a biological sample may be especially useful for diagnosing a cell proliferative disease or an increased likelihood of such a disease, particularly in a human subject, using a HIF-3α nucleic acid probe or HIF-3α antibody. The present inventor also suspect that there exist a correlation between the degree of malignancy of certain types of tumor with the amount HIF-3α or fragment thereof, and that high levels of HIF-3α is indicative that the tumoral cells have a higher angiogenesis activity and malignancy. Highly malignant cancers are cancers which cells display a short doubling time (e.g. hematopoietic cancer, lung cancers, prostate cancer, testis cancer, breast cancer, melanomas, pancreatic cancer intestine cancers, sarcomas, prostate cancer and hematologic cancers).

The methods of the invention may be carried out by contacting, in vitro or in vivo, a biological sample (such as a blood sample or a tissue biopsy) from an individual suspected of harboring cancer cells, with a HIF-3α antibody or a probe according to the invention, in order to evaluate the amount of HIF-3α in the sample or the cells therein. The measured amount would be indicative of the probability of the subject of having proliferating tumoral cells since it is expected that these cells have a higher level of HIF-3α expression.

In a related aspect, the invention features a method for detecting the expression of HIF-3α in tissues comprising, i) providing a tissue or cellular sample; ii) incubating said sample with an anti-HIF-3α polyclonal or monoclonal antibody; and iii) visualizing the distribution of HIF-3α.

Assay kits for determining the amount of HIF-3α in a sample would also be useful and are within the scope of the present invention. Such a kit would preferably comprise HIF-3α antibody(ies) or probe(s) according to the invention and at least one element selected from the group consisting of instructions for using the kit, assay tubes, enzymes, reagents or reaction buffer(s), enzyme(s).

x) Identification of Molecules that Modulate HIF-3α Protein Expression

HIF-3α cDNA may be used to facilitate the identification of molecules that increase or decrease HIF-3α expression. In one approach, candidate molecules are added, in varying concentration, to the culture medium of cells expressing HIF-3α mRNA. HIF-3α expression is then measured (or expression of another gene, such as VEGF which expression is regulated by HIF-3α), for example, by Northern blot analysis using a HIF-3α cDNA, or cDNA or RNA fragment, as a hybridization probe. The level of HIF-3α expression in the presence of the candidate molecule is compared to the level of HIF-3α expression in the absence of the candidate molecule, all other factors (e.g. cell type and culture conditions) being equal.

Compounds that modulate the level of HIF-3α may be purified, or substantially purified, or may be one component of a mixture of compounds such as an extract or supernatant obtained from cells (Ausubel et al., supra). In an assay of a mixture of compounds, HIF-3α expression is tested against progressively smaller subsets of the compound pool (e.g., produced by standard purification techniques such as HPLC or FPLC) until a single compound or minimal number of effective compounds is demonstrated to modulate HIF-3α expression.

Compounds may also be screened for their ability to modulate HIF-3α-biological activity (e.g. VEGF expression, induction of angiogenesis). In this approach, the biological activity of HIF-3α or of a cell expressing HIF-3α (e.g. lung or kidney cell) in the presence of a candidate compound is compared to the biological activity in its absence, under equivalent conditions. Again, the screen may begin with a pool of candidate compounds, from which one or more useful modulator compounds are isolated in a step-wise fashion. The HIF-3α or cell biological activity may be measured by any suitable standard assay.

The effect of candidate molecules on HIF-3α-biological activity may, instead, be measured at the level of translation by using the general approach described above with standard protein detection techniques, such as Western blotting or immunoprecipitation with a HIF-3α-specific antibody (for example, the HIF-3α antibody described herein).

Another method for detecting compounds that modulate the activity of HIF-3α is to screen for compounds that interact physically with a given HIF-3α polypeptide. Depending on the nature of the compounds to be tested, the binding interaction may be measured using methods such as enzyme-linked immunosorbent assays (ELISA), filter binding assays, FRET assays, scintillation proximity assays, microscopic visualization, immunostaining of the cells, in situ hybridization, PCR, etc.

A molecule that promotes an increase in HIF-3α expression or HIF-3α activity is considered particularly useful to the invention; such a molecule may be used, for example, as a therapeutic to increase cellular levels of HIF-3α and thereby exploit the ability of HIF-3α polypeptides to promote and/or induce angiogenesis.

A molecule that decreases HIF-3α activity (e.g., by decreasing HIF-3α gene expression or polypeptide activity) may be used to decrease and/or block angiogenesis and/or cellular proliferation. This would be advantageous in the treatment of cancer.

Molecules that are found, by the methods described above, to effectively modulate HIF-3α gene expression or polypeptide activity, may be tested further in animal models. If they continue to function successfully in an in vivo setting, they may be used as therapeutics to either promotes or inhibit angiogenesis.

xi) Induction of Expression of Angiogenesis-Related Gene(s) by HIF-2α and HIF-3α

According to a related aspect, the present invention relates to methods and cells for inducing angiogenesis and for improving muscular function, and more particularly for treating coronary and cardiac diseases in mammals. The invention also provides genetically modified muscular cells expressing a plurality of angiogenesis-related genes.

This aspect of the invention is based on the use of a nucleotide sequence encoding a transcription factor from the hypoxia inducible factors family (HIF-1α, HIF-2α, and HIF-3α). As it will be shown in the exemplification section, the present inventors have demonstrated that HIF-2α was stimulating, in addition to VEGF, the expression of other molecules implicated in angiogenesis such as IL-8, IL-6, PlGF, LIF receptor, PAI-2 and MMP7 in muscular cells. The inventors showed, in a model of rat CHF, that HIF-2α could be used for therapeutic angiogenesis in mammals. Also, the inventors have genetically modified skeletal muscle cells (SkMC) with HIF-2α gene and showed that these cells demonstrated superior angiogenic properties in vivo. Furthermore, treatment of CHF rats with HIF-2α gene transfer resulted in angiogenesis, higher metabolic activity and improved cardiac functions.

Since HIF-1α, HIF-2α, and HIF-3α belong to the same family and are closely related, it is expected that similar results could be obtained with any of the HIF members. Therefore, the additional aspects of the present invention given in the present section encompasses not only the use of HIF-2α but HIF-1α and HIF-3α (all isoforms) as well. HIF-1α (GenBank™ accession No. U22431) is described in by Wang et al., (*Proc. Natl. Aca. Sci. USA* (1995) 92: 5510-5514) and in U.S. Pat. Nos. 5,882,314; 6,020,462 and 6,124,131. HIF-2α (GenBank™ accession No. U81984) is described by Tian et al., (*Genes & Dev.* (1996) 11: 72-82), and in U.S. Pat. No. 5,692,963. One isoform of HIF-3α is described herein and another isoform (GenBank™ accession No. AB054067) has been described by Hara et al. (*Biochem. Biophys. Res. Comm.* (2001), October 5; 287:808-813). All these documents are incorporated herein by reference.

Therefore, this aspect of the invention is directed to a method for inducing in a muscular mammalian cell the expression of at least one, preferably a plurality of angiogenesis-related gene(s), the method comprising the step of introducing the cell a nucleic acid sequence encoding a functional HIF-2α transcription factor or a functional HIF-3α transcription factor.

According to another related aspect, the invention is directed to a method for increasing the metabolic activity of a muscular cell (such as glucose consumption), comprising the step of introducing and expressing in the cell a nucleic acid sequence encoding a functional transcription factor of the Hypoxia Inducible Factor (HIF) family. Preferably, the transcription factor is HIF-2α or HIF-3α.

In a further related aspect, the invention is directed to a method for improving cardiac tissue functions of a mammal, comprising the step of providing to the cardiac tissue of the mammal a plurality of genetically modified cells expressing a nucleic acid sequence encoding a functional HIF-2α transcription factor or a functional HIF-3α transcription factor.

According to another related aspect, the invention is directed to a method for inducing angiogenesis in a mammalian muscular tissue, comprising the step of providing the muscular tissue with a plurality of genetically modified muscular cells expressing a nucleic acid sequence encoding a functional HIF-2α transcription factor or a functional HIF-3α transcription factor.

According to the invention, a nucleotide sequence encoding a transcription factor of hypoxia inducible factor family is introduced and expressed into a muscular cell, preferably a skeletal muscular cell or a cardiac cell by using any suitable method including but not limited to adenoviral infection, and plasmid, cosmid or artificial chromosome transfection or electroporation. More preferably, the nucleic acid sequence encoding the transcription factor(s) is a cDNA.

In a further aspect, the invention is directed to a genetically modified muscular cell (e.g. skeletal muscle cell, cardiac cell) expressing a functional HIF-2α transcription factor or a functional HIF-3α transcription factor. Preferably, the cell is a skeletal muscular cell or a cardiac cell. Preferably also, the cell comprises a cDNA encoding the transcription factor. As mentioned previously, such cells may be particularly useful when transplanted in a compatible recipient for inducing angiogenesis, relieving ischemia, increasing the metabolic activity of a mammalian muscular tissue, and/or increasing muscular function in CHF or in peripheral vascular disease, locally or in surrounding transplanted tissue. Of course, the genetically modified cells of the present invention could also be used for the formation of artificial organs or for tissue constructions.

Although transplantation of cells (autologous transplantation or from a compatible donor) is preferred for inducing angiogenesis locally, in surrounding tissue and/or for improving the metabolic activity of a muscular cell and/or for relieving ischemia in coronary heart disease or in peripheral vascular disease and/or for improving the mammal's cardiac functions, the nucleic acid sequence encoding the functional transcription factor may be introduced directly in the tissue of the mammal using any suitable method known in the art (see hereinbefore for some examples). The angiogenesis-related gene should be expressed at a level that is sufficient to induce angiogenesis locally or in surrounding tissue.

As it will now be demonstrated by way of an example hereinafter, the present invention is useful for inducing angiogenesis, relieving ischemia and increasing cell metabolic activity and tissue function in CHD and in PVD.

EXAMPLES

The following examples are illustrative of the wide range of applicability of the present invention and is not intended to limit its scope. Modifications and variations can be made therein without departing from the spirit and scope of the invention. Although any method and material similar or equivalent to those described herein can be used in the practice for testing of the present invention, the preferred methods and materials are described.

Example 1

Use of HIF-1α, HIF-2α and HIF-3α for Inducing Angiogenesis and Improving Muscular Functions Materials and Methods
Plasmids Construction HIF-1α-VP16/pcDNA3 was obtained from S. L. McKnight (Tian et al., Genes & Dev. (1996) 11:72-82). To generate HIF-1α-VP16/pcDNA3, a VP16 fragment (NheI and blunt ended EcoRI from pVP16 (ClonTech)) was inserted in HIF-1α/pcDNA3 cut with AflII and XbaI blunt ended in presence of a NheI-AflII linker composed of the oligos TTA AGA TAT CGA TGA CAC GTG (SEQ ID NO:4) and TCA GCA CGT GTC ATC GAT ATC (SEQ ID NO:5), replacing the 3' part of HIF-1α sequence by VP16, putting DNA binding domain and heterodimerization domains (HLH and PAS) of HIF-1α (encoded by the 5' of the gene) in frame with VP16 transcription activation domain.

HIF-2α-VP16/pcDNA3 was obtained from S. L. McKnight (Tian et al., Genes & Dev. (1996) 11:72-82). To generate HIF-2α-VP16/pcDNA3, a HIF-2α 5' region was amplified by PCR using HIF-2α/pcDNA3 as template with the oligonucleotides T7 and GCT AGC TAG GAA GTT ACT CCT CTC (SEQ ID NO:6), creating a NheI at the end of HIF-2α DNA binding domain and heterodimerization domains (HLH-PAS). This fragment was cut with NheI and KpnI and was inserted in place of HIF-1α sequence in HIF-1-VP16/pcDNA3 cut NheI and KpnI. Sequencing confirmed integrity of the amplified sequence.

HIF-3α was cloned by RT-PCR by homology deduction from mouse HIF-3α sequence. Using Marathon™ RT-PCR kit (ClonTech), 2 fragments of HIF-3α sequence were amplified from adult human heart RNA (ClonTech) with the oligos CCA TGG ACA GGT CGA CCA CGG AGC TGC GCA AGG (SEQ ID NO:7) (containing an ATG initiator in a NcoI site) and CGC AGG CAG GTG GCT TGT AGG CCC T (SEQ ID NO:8) for the 5' end and with the oligos CAG CTG GAG CTC ATT GGA CAC AGC ATC (SEQ ID NO:9) and CCC CAT CCT GTG CGT TGG CTG CCG (SEQ ID NO:10) for the 3' end. Both fragments were sequenced and put together with the unique NdeI site, and the reconstructed cDNA was inserted in the NcoI initiator of HIF-1α/pcDNA3, using HIF-1α Kozak sequence to initiate translation. To generate HIF-3α-VP16/pcDNA3, a PCR fragment containing HIF-3α DNA binding domain and heterodimerization domains (HLH and PAS) was amplified using HIF-3α/pcDNA3 as template with the oligos T7 and GGA GTC AGC TTA AGC TGA ATG GGT CTG C (SEQ ID NO:11). The amplification product was cut with BamHI and AflII (coming from the 3' oligo) and inserted in place of HIF-1α sequence in HIF-1α-VP16/pcDNA3 cut with BamHI and AflII. Sequencing confirmed integrity of the amplified sequence.

Transfection

Early passage 293 cells (ATCC # CRL-157) were plated at $1.7 \times 10^6$ cells per plate (100 mm) and grown overnight. 10 µg of sterile plasmid DNA was transfected with lipofectamin, according to the instructions from the manufacturer. After a 5 hours transfection, cells were incubated either in normoxia (5% $CO_2$ in normal air at 37° C.) or in hypoxia (5% $CO_2$, 2%

$O_2$ at 37° C.) for 24 hours. ~70% confluence Hep3B cells (ATCC #HB-8064) in 100 mm dishes were transfected with 4 μg of sterile plasmid DNA with 6 μl of Fugene 6™ (Roche), according to the instructions from the manufacturer.

Adenovirus Production

HIF constructs were used to produce adenoviral vectors with the Ad.EaSy™ technology using manufacturer methodology (Q-Biogene).

Infection

Early passage human SkMC (Cambrex #CC-2561) were plated in 100 mm dishes and grown until they reached ~70% confluence. Cells were rinsed with PBS and covered with 4 ml DMEM with 10% fetal calf serum (FCS) and adenoviruses at a MOI of 500. This MOI allow infection of only ~10% of the cells. Cells were incubated at 37° C. with constant but gentle agitation for 6 hours. 6 ml of DMEM with 10% FCS was added and cells were incubated overnight at 37° C. Cells were then incubated either in normoxia (5% CO2 in normal air at 37° C.) or in hypoxia (5% CO2, 2% O2 at 37° C.) for 24 hours.

RNAses Protection Assay (RPA)

Total RNA was isolated from transduced cells by Guanidine thiocyanate-phenol extractions as described (Staffa, A., et al., *J. Biol. Chem.* (1997) 272: 33394-401) (FIG. 3A or 3C) or with Rneasy Mini Kit™ (Qiagen) as described by the manufacturer. 15 μg total RNA per sample were analyzed by RPA using RPA III kit (Ambion). Probe were prepared from hAngio1 template set (Pharmingens) for FIG. 3A or from home made VEGF and actin template for the others. VEGF template was prepared by amplification on the phVEGF165.5R (from J. F. Isner) (Tsurumi, Y., et al., *Circulation.* (1996) 94: 3281-3290) with the oligos CCG GM TTC TCT ACC TCC ACC ATG CC (SEQ ID NO:12) and CCG GAA TTC CTC AGT GGG CAC ACA CTC C (SEQ ID NO:13), digestion of the amplification product with EcoRI (in both oligos) and insertion in pBluescript cut with EcoRI. Sequence integrity was confirmed by sequencing. The resulting plasmid was digested with HindIII and transcribed with T7 RNA polymerase to generate an antisense RNA probe. Actin probe template was obtained from W. E. Bradley (Houle, B., et al., *Proc. Natl. Aca. Sci. USA* (1993) 90: 985-989).

Quantification

Autoradiograms were scanned on an Alpha Imager 2000™ (Alpha Innotech Corporation). Intensity of each band was measured and relative expression was calculated as VEGF intensity/Flt4 intensity for FIG. 3A or as VEGF intensity/actin intensity for the others. Relative VEGF values were then normalized so that a value of 100 was attributed to the control samples in normoxia. Protein VEGF produced were proportional to the amount of mRNA quantified. Results are expressed as mean±SED.

Gene Chip Hybridization

Total RNA was isolated from human SkMC (Clonetics) infected with either Ad.Null™ (Q-Biogene) or Ad.HIF-2α as described (Staffa, et al., *J. Biol. Chem.* (1997) 272: 33394-401). Probes were prepared and hybridized to Atlas Human 1.2 Array™ (Clontech) with ExpressHyb™ solution (Clontech) according to the instructions from the manufacturer. The arrays were exposed to phosphorimager screen and analyzed with the Atlas 2.01 ™ software (Clontech).

Angiogenesis In Vivo

Early passage human SkMC (uninfected or infected with the indicated adenovirus vectors) were incorporated into matrigel (50000 cells/0.5 ml) and injected subcutaneously into skid mice (10 per groups). Matrigel alone or bFGF (400 ng/ml) were used as controls. 7 days post-implantation, matrigel plugs were excised and processed for histological evaluation. Each measurement corresponds to the degree of cellular response in a microscopic field expressed as Integrated Density (sum of the gray values in the selection, with the background subtracted, 6 measurements on each plug).

Metabolic activity in infarcted rats created by a permanent left anterior descending coronary artery ligation (Myoinfarct™ rats, Charles River Laboratories) was measured 5 days post ligature by injection of $^{18}$FDG (~750 μCi/100 g) and dynamic acquisition using a small animal PET-Scan™ (Sherbrooke University). Ten days after the ligature, a mini-thoracotomy was performed to inject a solution of Ad.HIF2α/VP16 or saline (N=2) in the infarcted area of the left ventricle. Another $^{18}$FDG PET-Scan™ was performed 14, 28, 42 and 56 days after the injection. Metabolic activity was calculated as the amount of $^{18}$FDG found in an area of the lateral wall of the left ventricle, where the infarct is localized, normalized with the amount of FGD found in an unaffected area in the septal wall that is irrigated by another coronary artery. After the last PET-scan™, animals were sacrificed and blood vessels were quantified in the entire infarcted area or in the fields of the margins between healthy and infarcted tissues.

Results

In Vitro VEGF Induction by HIF-1α, HIF-2α and HIF-3α

FIGS. 2A, 2B, 3A, 3B and 3C illustrate the expression of angiogenesis related genes in human cells transfected with HIF constructs.

The natural (wild type) form of HIF factors or activated version were introduced in pcDNA3 (Invitrogen Corp.), an expression vector. Activated constructs consist in the deletion of hypoxia regulated instability domains located in the N' part of the proteins and the introduction of a strong activator of transcription, the VP16 domain from Herpes virus (Vincent et al., *Circulation* (2000) 102: 2255-2261). The resulting hybrids are no longer regulated by hypoxia and always display a transactivation activity.

These plasmids were transiently transfected in human embryonic kidney 293 cells (HEK293) or in human liver cells Hep3B. Cells were incubated 24 hours either in normoxia (normal conditions) or in hypoxia (2% oxygen) and total RNA was isolated. Similarly, human skeletal muscle cells (hSkMC) were transduced with adenovirus vectors expressing some of the HIF constructs. Endogenous VEGF gene activation following HIF constructs transfection was analyzed by RNAse Protection Assay (RPA, Ambion).

Figure 2A:
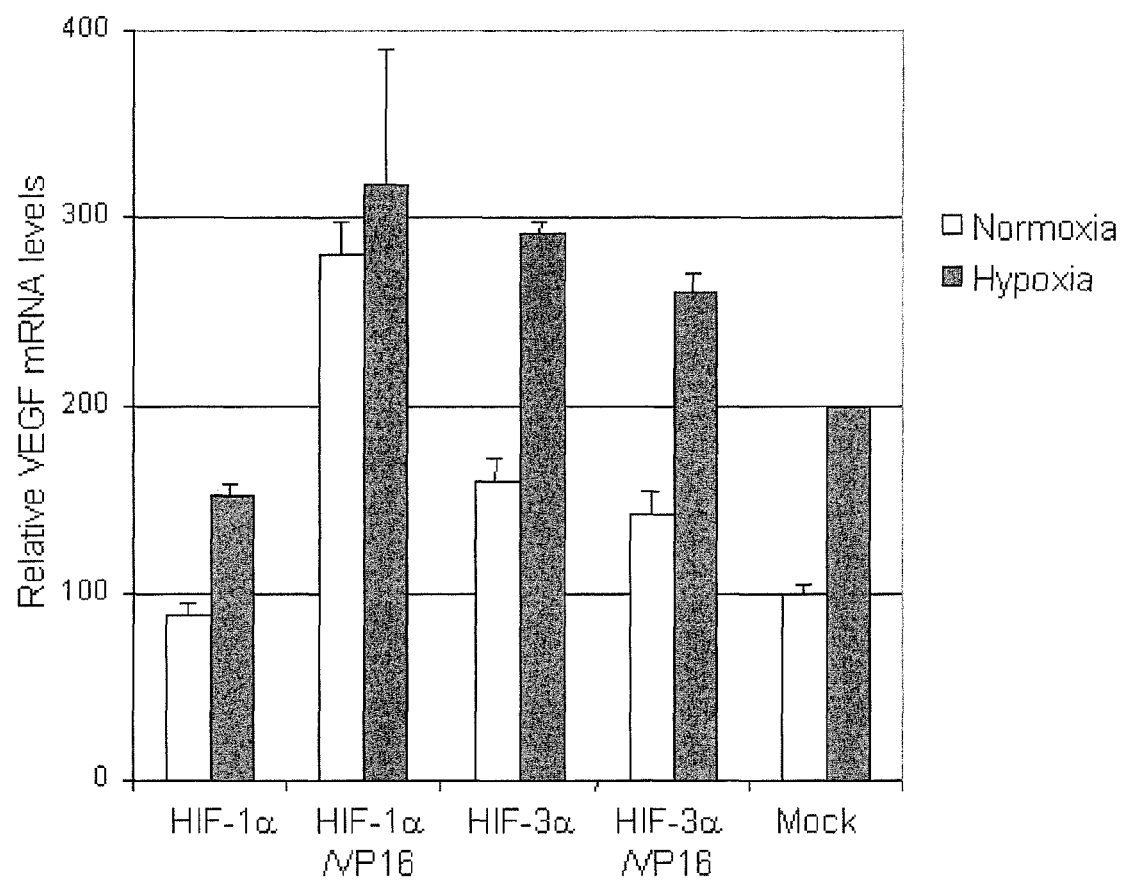
FIG. 2A is a bar graph illustrating the expression of VEGF in HEK293 cells transfected with HIF-3α constructs.
Figure 2B:
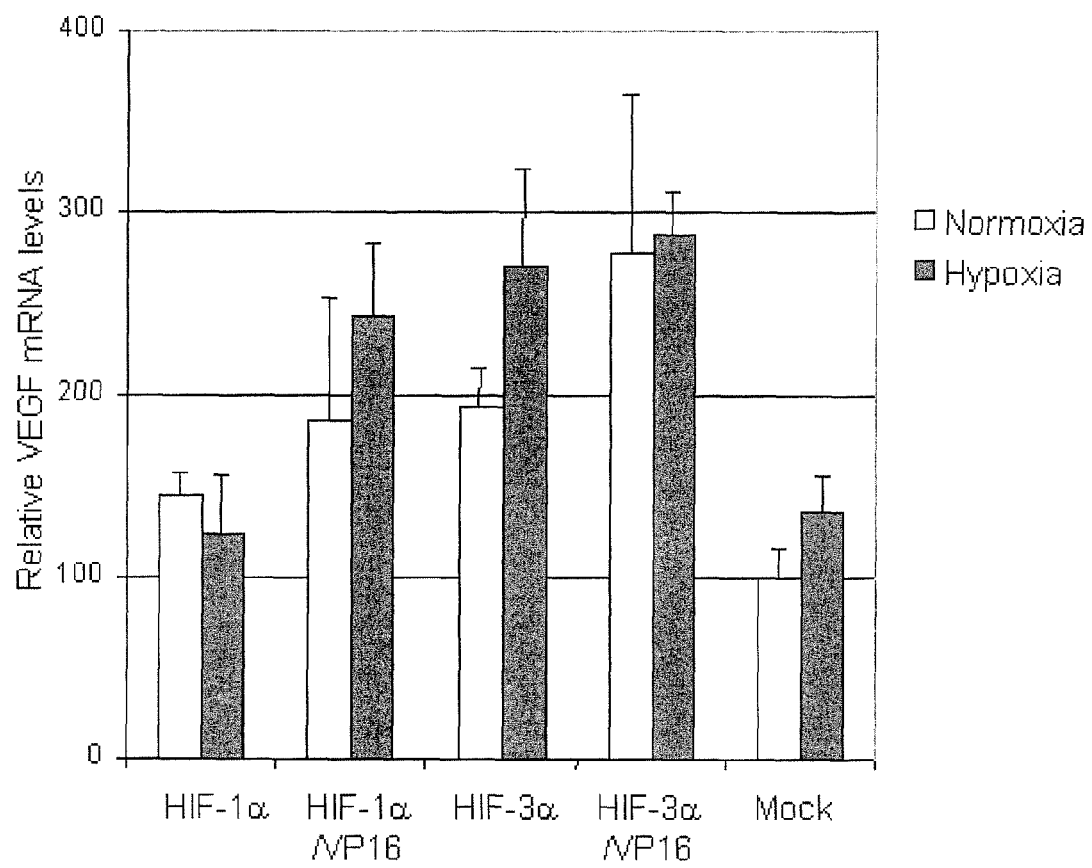
FIG. 2B is a bar graph illustrating the expression of VEGF in Hep3B cells transfected with HIF-3α constructs

No VEGF induction was produced by HIF-1α transfection in normoxia (similar to control) (FIGS. 2A, 2B, 3A and 3B). This result was expected since HIF-1α is quickly degraded in normoxia. The HIF-1α/VP16 hybrid stimulated VEGF both in normoxia and hypoxia, since the protein is no longer regulated by oxygen tension. Interestingly, HIF-3α was very efficient to stimulate VEGF in HEK293 and Hep3B cells (FIGS. 2A and 2B). The levels were superior to those obtained with HIF-1α both in normoxia and in hypoxia, although HIF-1α/VP16 had an even higher transactivation activity. The activation of HIF-3α with the VP16 domain did not significantly modify the levels of VEGF induction.

Figure 3A:
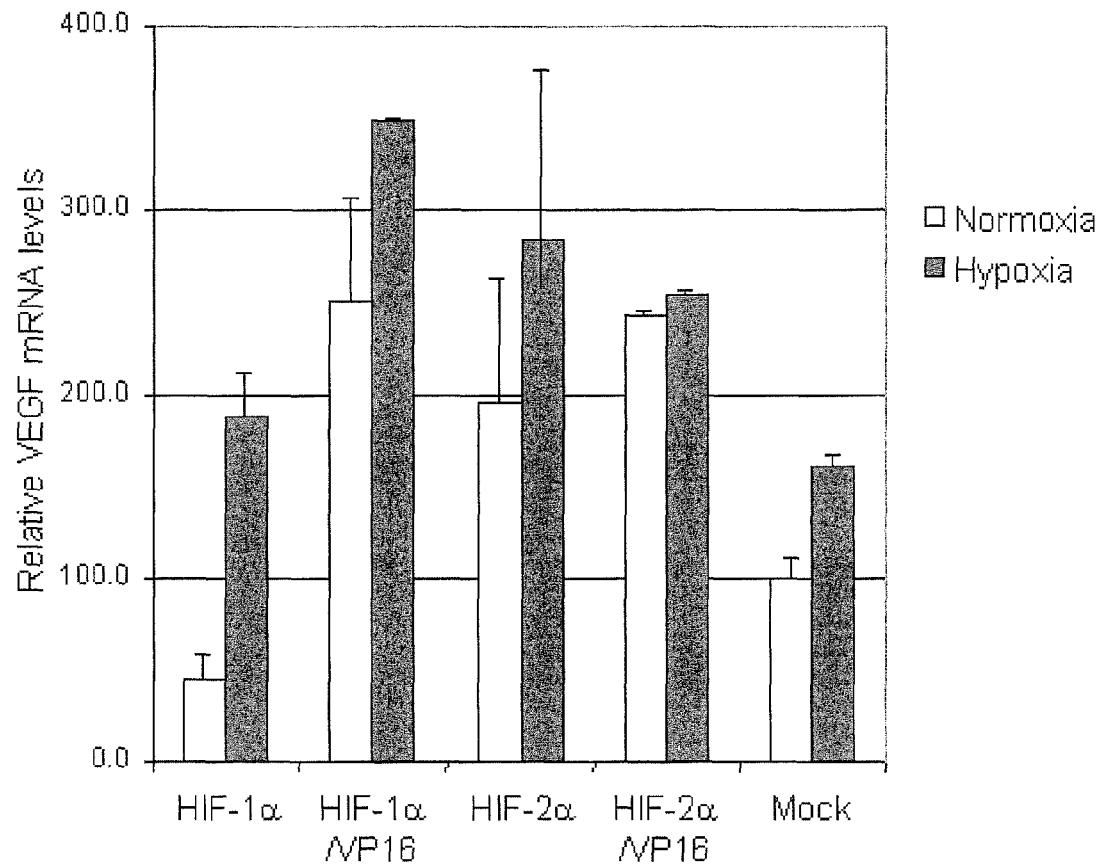
FIG. 3A is a bar graph illustrating the expression of VEGF in HEK293 cells transfected with HIF-2α constructs.
Figure 3B:
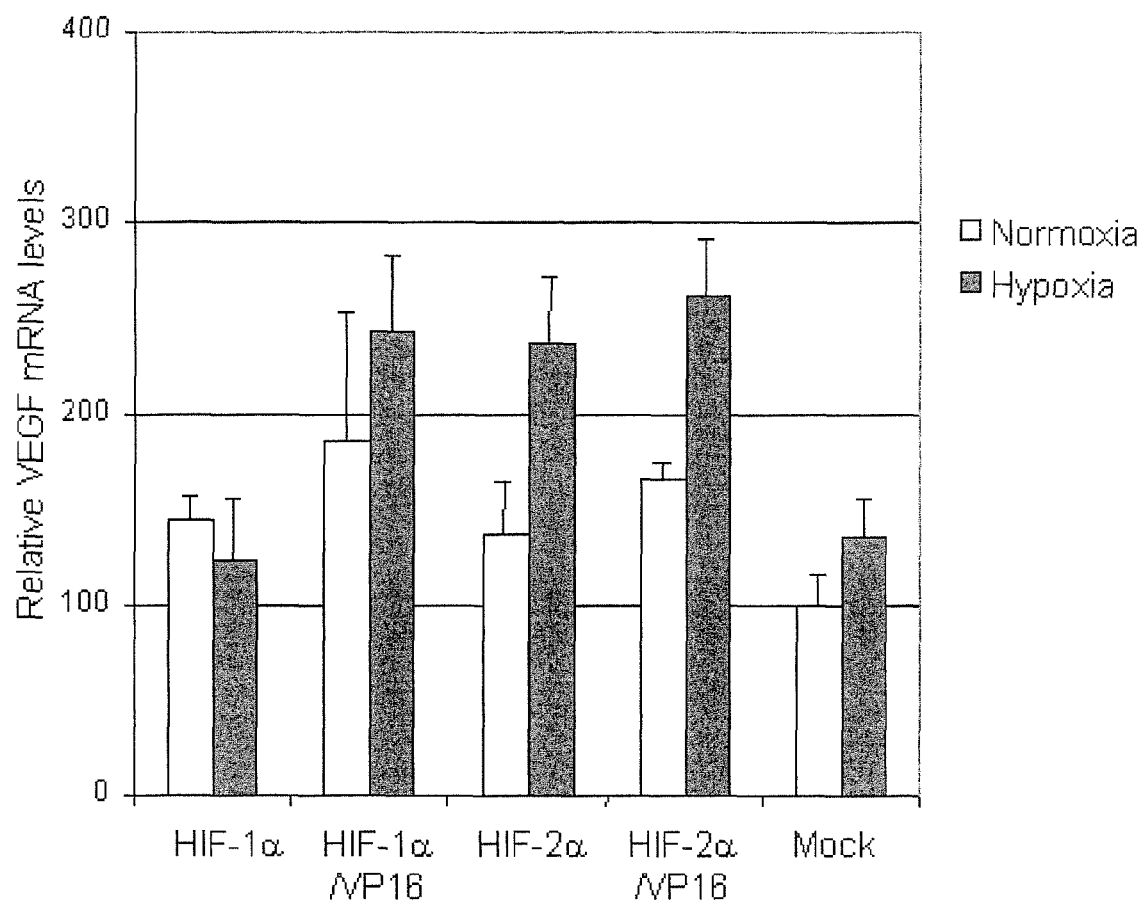
FIG. 3B is a bar graph illustrating the expression of VEGF in Hep3B cells transfected with HIF-2α constructs.
Figure 3C:
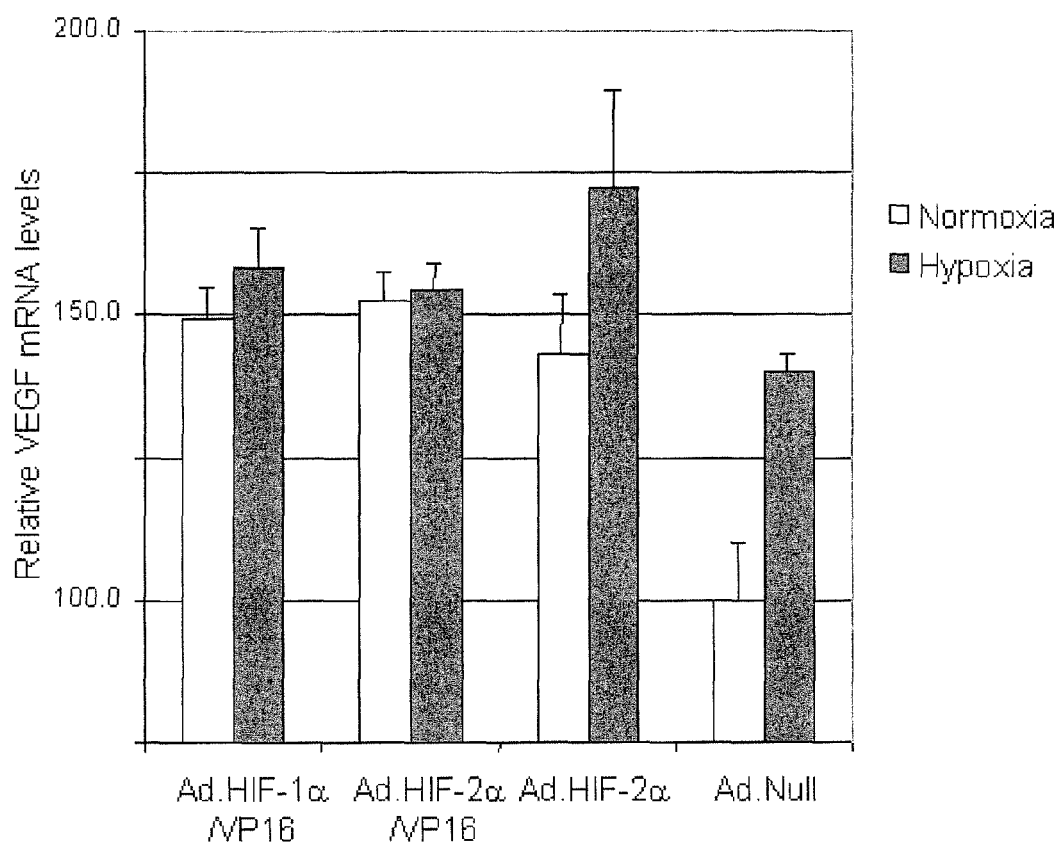
FIG. 3C is a bar graph illustrating the expression of VEGF in human skeletal muscle cells transduced with HIF-2α constructs.

VEGF stimulation by HIF-2α was also very important. FIGS. 3A, 3B and 3C show that the wild type version of the protein stimulated VEGF in ranges comparable to HIF-1α/VP16, both in normoxia and in hypoxia, in the 3 cells types studied (HEK293 in FIG. 3A, Hep3B in FIG. 3B and hSKMC in FIG. 3C). The VP16 fusion did not provide an important advantage in the levels of VEGF produced.

Activation of Angiogenic Genes by HIF-2α In Vitro

Figure 4:
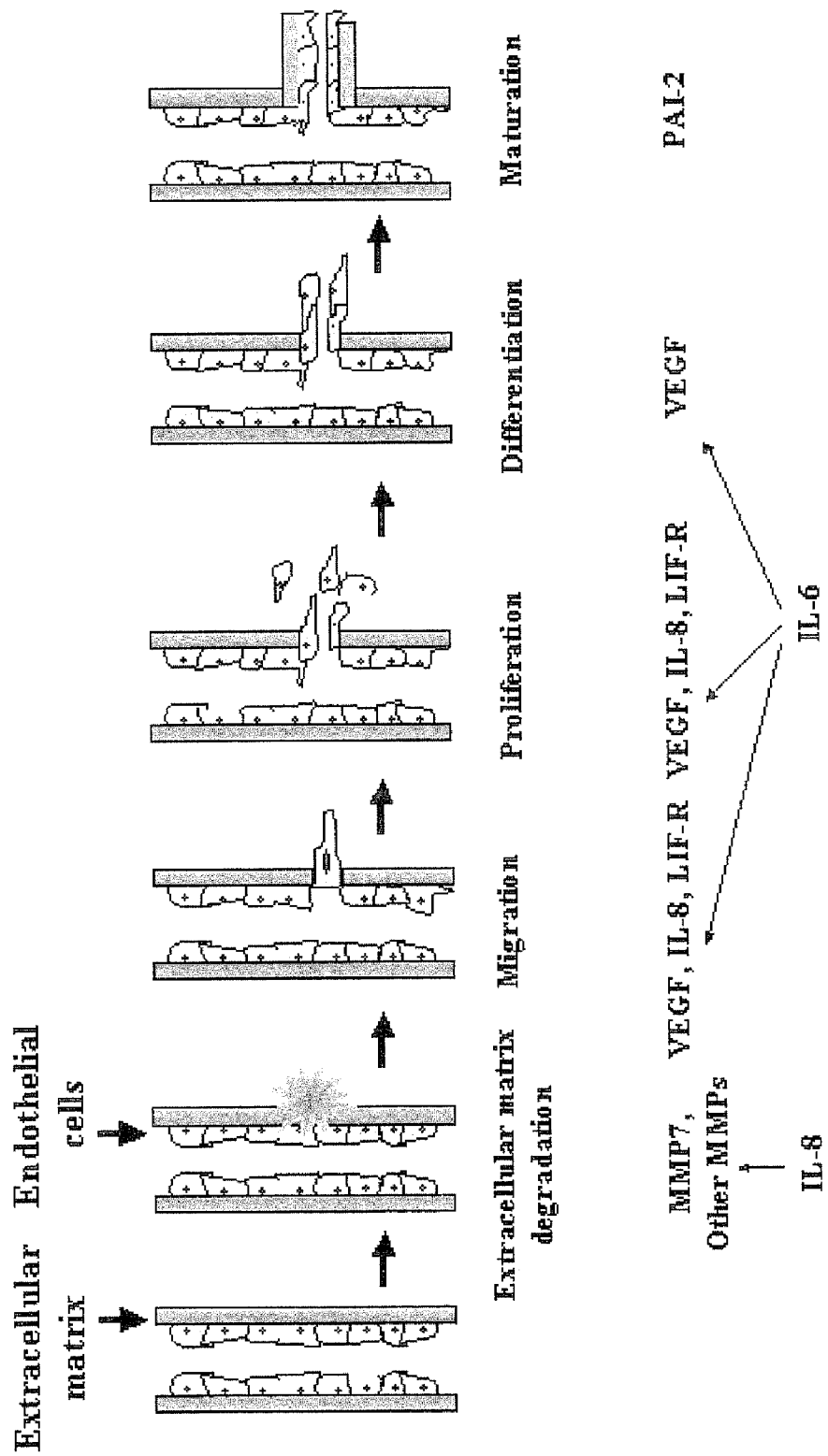
FIG. 4 is a schema showing a possible process of angiogenesis and the probable role therein of some angiogenesis-related genes.

VEGF is an important angiogenic gene. However, angiogenesis is a complex process involving several steps that are regulated by several factors. To evaluate HIF factors potential as an angiogenic modulator, gene expression was compared in human SkMC infected either with Ad.HIF2α or Ad.Null™ using gene chip technology. cDNA probes derived from either cell population was hybridized on a Atlas Human 1.2 Array™ (Clontech) assessing expression of almost 1200 genes. Of the genes differentially regulated, VEGF was the one showing the most significant increase. VEGF stimulates both proliferation, migration and differentiation of endothelial cells. Interestingly, other angiogenic genes were activated (Table 2). As VEGF, Interleukin-8 (IL-8) and the activation of Leukemia Inhibitory Factor Receptor (LIF-R) are known to stimulate the proliferation of endothelial cells. However, IL-8 also acts by activating the release of metalloproteinases responsible for the basal membrane disruption, the first step of angiogenesis (FIG. 4). LIF is also known to enhance survival of SkMC, which would be useful in cell therapy. The role of Interleukin-6 (IL-6) is more indirect: it has no effect on endothelial cell proliferation, but stimulates their migration and differentiation. It is also an enhancer of VEGF production. Placental growth factor (PIGF) was shown to act in cooperation with VEGF to stimulate angiogenesis. Matrix metalloproteinase 7 (MMP7) is a potent proteinase able to initiate the angiogenesis process while placental plasminogen activator inhibitor 2 (PAI-2) is able to stabilize nascent vessels (FIG. 4). There are many other potential angiogenic factors that couldn't be detected in this assay because of limitations of the gene chip, but that might be induced by HIF factors.

TABLE 2

Genes activated by HIF-2α in SkMC.

| Gene | Fold induction | Category |
|---|---|---|
| VEGF | 9.10 | Growth factor |
| IL-8 | 2.26 | Growth factor |
| IL-6 | 2.21 | Growth factor |
| PIGF | Up* | Growth factor |
| LIF-R | Up* | Growth factor |
| PAI-2 | 1.93 | Proteinase inhibitor |
| MMP7 | Up* | Metalloproteinase |

*Inductions labeled "up" are representing the activation from a previously undetected gene.

HIF-2α Stimulates Angiogenesis In Vivo

Figure 5A:
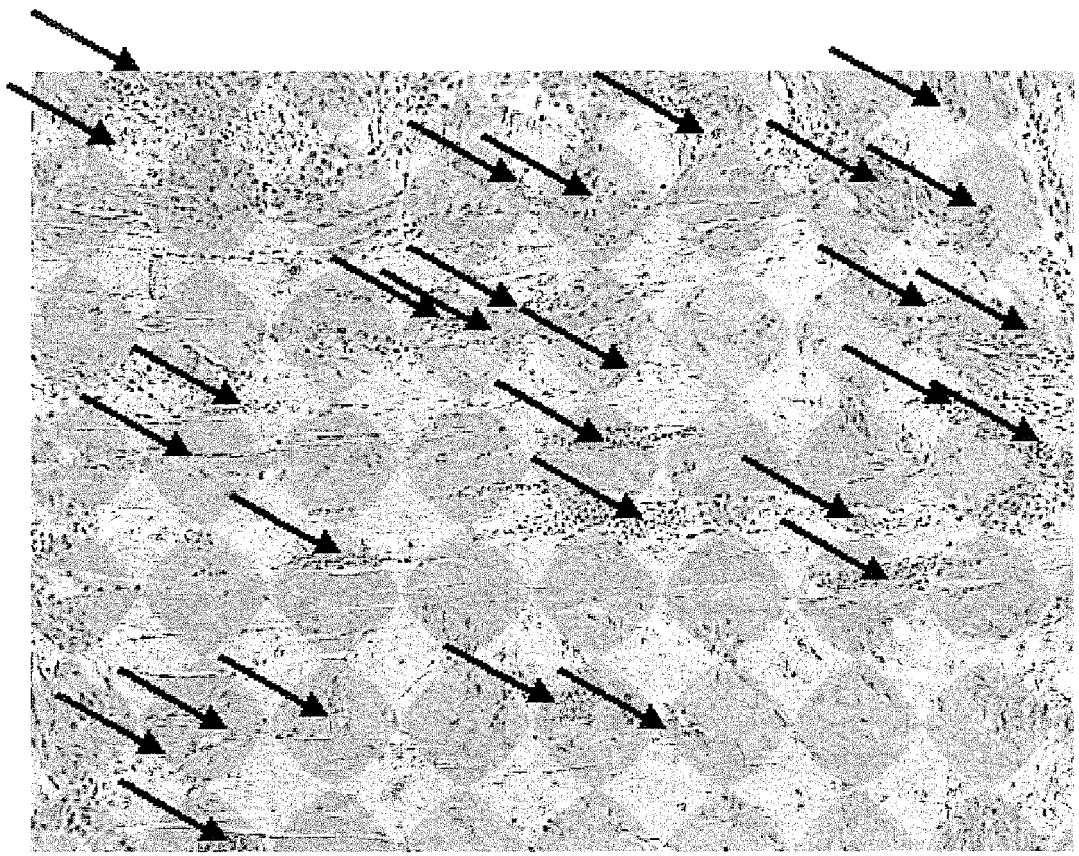
FIG. 5A is a photograph of HIF-2α modified hSkMC implanted subcutaneously in mice showing differentiation in myotubes and an organized vasculature around and in between muscle fiber (arrows point to vessels).
Figure 5B:
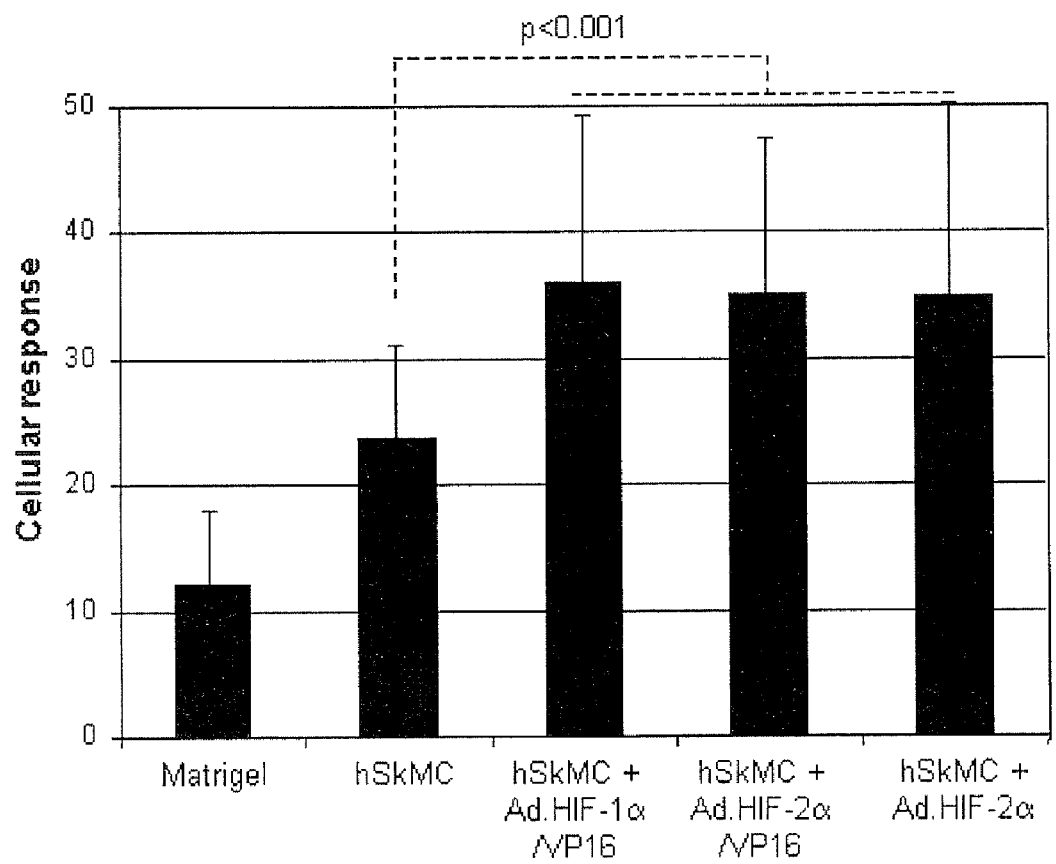
FIG. 5B is a bar graph that shows the angiogenic activity of HIF constructs modified hSkMC.

Angiogenic potential of HIF constructs were evaluated in vivo by subcutaneous implantation of SkMC transfected with HIF constructs in mice. Seven days following implantation, modified cells pellets showed significantly higher blood vessel density than unmodified SkMC (FIG. 5B). This result confirms that the VP16 activation is not necessary in the case of HIF-2α. Modified SkMC differentiated in vivo into myotubes supported by extracellular matrix and surrounded by new blood vessels (FIG. 5A). The angiogenesis was important around the myotubes and appeared well organized.

Figure 6A:
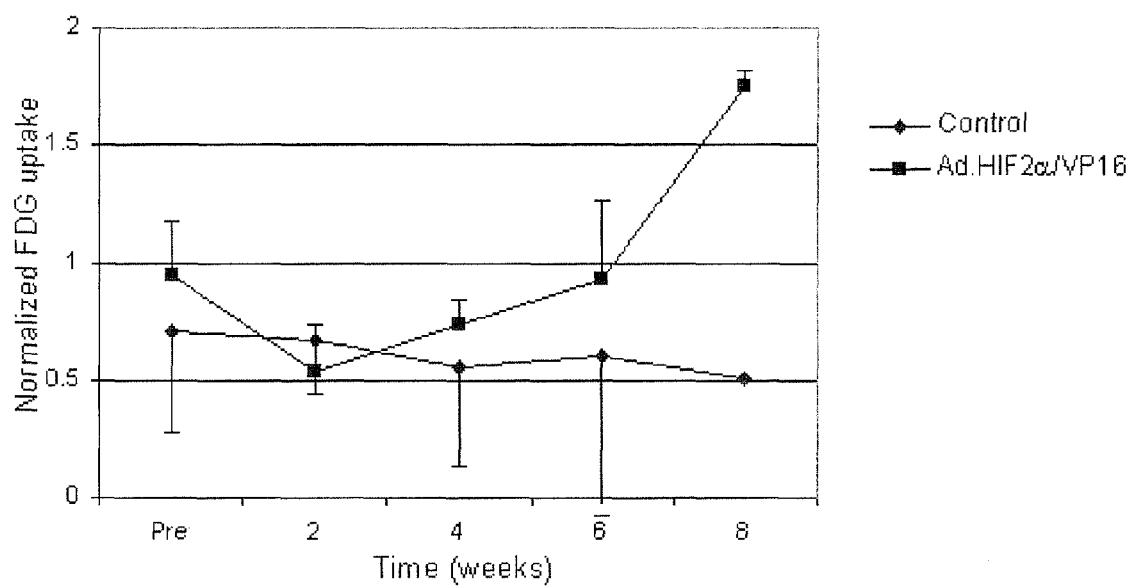
FIG. 6A is a graphic showing the metabolic activity in an ischemic rat heart muscle treated with Ad.HIF-2α.
Figure 6B:
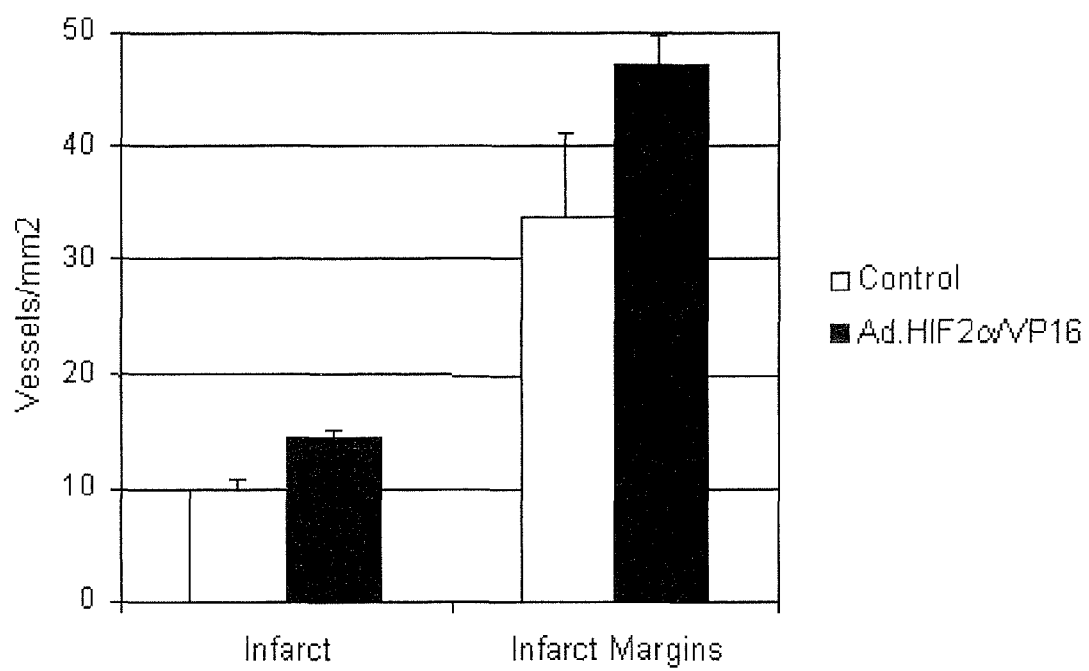
FIG. 6B is a bar graph that shows the measured blood vessel density in the infracted area treated with myocardial HIF-2α gene transfer in rats.

HIF-2α was also directly delivered in a model of MI in rats. Metabolic activity was assayed 5 days before direct myocardial injection of the vector Ad.HIF-2α/VP16 and at several time points in the following 2 months. As shown in FIGS. 6A and 6B, an improved metabolic activity was measured in the infarcted area of treated rats over control ones as quantified by position emission tomography-scan (PET-Scan™). When blood vessel density was quantified by histology, an increase number of blood vessels was noted for the adenovirus treated rats in the infarcted area, as well as in the peri-infarcted zone (FIG. 6B).

3) Discussion

In vitro transfection experiments showed that wild type HIF-3α and HIF-2α were superior to HIF-1α to induce VEGF. Used in gene therapy, HIF-3α would thus be very useful to modulate angiogenesis.

As shown in FIGS. 2A, 2B, 3A, 3B and 3C, transfection of HIF-VP16 fusion encoding constructs resulted in a significant stimulation of VEGF. However, in gene therapy in humans, these constructs pose the problem of immunogenicity. The presence of the VP16 sequence, of viral origin, is recognized by the immune system and trigger an immune response against the transferred gene. Construct using wild type human genes, such as HIF-3α, has the advantage of being less immunogenic, thus providing a longer period of expression. In comparison, HIF-1α had a poor angiogenic potential in normoxia and requires the VP16 modification to be fully active (FIGS. 2, 3 and Vincent et al., *Circulation* (2000) 102: 2255-2261). FIGS. 2A, 2B, 3A, 3B and 3C also strongly suggest that HIF-2α and HIF-3α could be used efficiently in gene transfer protocols to modify gene transcription of the targeted cells. In particular, VEGF expression is increased, which result in angiogenesis. It is thus proposed to use HIF-2α or HIF-3α sequence in ischemic diseases to increase blood vessels and blood perfusion.

The analysis of genes activated by HIF-2α revealed the induction of several angiogenic genes (Table I). These genes play a role in various aspects of angiogenesis (FIG. 4) and the resulting angiogenesis is thus expected to be strong and well organized. This is a major advantage compared to the use of solely VEGF to induce angiogenesis since all the key steps of angiogenesis will be stimulated. It is expected that HIF-3α will also regulate several angiogenesis related genes, and possibly the same ones as HIF-2α.

In vivo experiments proved that HIF-2α gene transfer resulted in a significant angiogenesis, both in sub-cutaneous implants (FIG. 5B) and in a MI heart model (FIG. 6B). These results confirmed that the VP16 fusion was not necessary to result in the formation on blood vessels. This characteristic confers an important advantage to HIF-2α sequence as an angiogenic agent. The use of a native sequence in gene transfer therapy will raise a much lower immunogenic response than a construct with VP16, of viral origin. Since HIF-3α was also superior to HIF-1α and showed in vitro induction of VEGF similar to HIF-2α, it is expected that it will also be efficient in vivo.

Angiogenesis resulted in an increase in metabolic activity (increased glucose consumption) in the infarcted area as shown in FIG. 6A, indicating an improvement in the tissue function. This, higher blood supply translated in higher muscle activity which can improve heart pumping function.

In summary, it is clear that HIF factors delivered either directly or via an implanted cell, offers a great potential for myocardial regeneration and improvement of cardiac function.

The results reported herein constitute a proof of principle to the effect that HIF-2α and HIF-3α can be used in gene therapy.

While several embodiments of the invention have been described, it will be understood that the present invention is capable of further modifications, and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims.

What is claimed is:

1. An isolated or purified protein comprising an amino acid sequence selected from the group consisting of:
   a sequence having at least 95% identity to SEQ ID NO: 2 over the full length of SEQ ID NO:2;
   a sequence having at least 95% similarity to SEQ ID NO: 2 over the full length of SEQ ID NO:2;
   a sequence having at least 95% identity to amino acid sequences encoded by a nucleic acid sequence of SEQ ID NO: 3 over the full length of SEQ ID NO:3; and
   a sequence having at least 95% sequence similarity to amino acid sequences encoded by a nucleic acid sequence of SEQ ID NO: 3 over the full length of SEQ ID NO:3,
   wherein the isolated or purified protein induces VEGF expression.

2. The protein of claim 1, wherein inducement of VEGF expression promotes angiogenesis.

3. A composition comprising the isolated or purified protein of claim 1 and a pharmaceutically acceptable carrier.

* * * * *

UNITED STATES PATENT AND TRADEMARK OFFICE
CERTIFICATE OF CORRECTION

PATENT NO. : 8,088,893 B2  Page 1 of 1
APPLICATION NO. : 12/400955
DATED : January 3, 2012
INVENTOR(S) : Guy et al.

It is certified that error appears in the above-identified patent and that said Letters Patent is hereby corrected as shown below:

In the Patent:

Column 7, Line 6: Please correct "infracted" to read -- infarcted --

Column 14, Line 33: Please correct "v) Uregulation" to read -- v) Upregulation --

Column 23, Line 31: Please correct "CCG GM TTC" to read -- CCG GAA TTC --

Signed and Sealed this
Fifteenth Day of May, 2012

David J. Kappos
*Director of the United States Patent and Trademark Office*